(12) United States Patent
Li et al.

(10) Patent No.: US 11,109,794 B2
(45) Date of Patent: Sep. 7, 2021

(54) METHOD AND APPARATUS FOR PROCESSING ECG SIGNALS, AND ECG MACHINE

(71) Applicant: BOE TECHNOLOGY GROUP CO., LTD., Beijing (CN)

(72) Inventors: Guangfei Li, Beijing (CN); Qi Yang, Beijing (CN); Xun Zhang, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 160 days.

(21) Appl. No.: 16/414,523

(22) Filed: May 16, 2019

(65) Prior Publication Data

US 2019/0365268 A1    Dec. 5, 2019

(30) Foreign Application Priority Data

May 30, 2018    (CN) .......................... 201810543088.X

(51) Int. Cl.
*A61B 5/352*    (2021.01)
*A61B 5/00*    (2006.01)
(Continued)

(52) U.S. Cl.
CPC .............. *A61B 5/352* (2021.01); *A61B 5/333* (2021.01); *A61B 5/366* (2021.01); *A61B 5/7203* (2013.01); *A61B 5/726* (2013.01)

(58) Field of Classification Search
CPC ... A61B 5/0456; A61B 5/0432; A61B 5/0472; A61B 5/7203; A61B 5/726;
(Continued)

(56) References Cited

U.S. PATENT DOCUMENTS 6,609,023 B1 *  8/2003  Fischell .............. A61B 5/0031
                                                    600/515
2004/0049120 A1 * 3/2004  Cao ..................... A61B 5/0456
                                                    600/521
(Continued)

FOREIGN PATENT DOCUMENTS

CN    103083011 B  * 11/2014
CN    105212922 A    1/2016
(Continued)

OTHER PUBLICATIONS

Shang, Yu, et al., QRS Characteristic Waveform Extraction Based on Biothogonal B-Spline Wavelet, 2014, International Journal of Control and Automation—vol. 7 No. 1, pp. 95-106 (Year: 2014).*

(Continued)

*Primary Examiner* — Joseph M Dietrich
*Assistant Examiner* — Michael T. Holtzclaw
(74) *Attorney, Agent, or Firm* — McDermott Will and Emery LLP

(57) ABSTRACT

A method for processing ECG signals includes: removing peak position information of any R wave of a plurality of R waves in a plurality of ECG signals if it is determined that a first RR interval is less than or equal to a first RR interval threshold, and an amplitude of the R wave is less than or equal to a first R wave amplitude threshold; and detecting at least one new R wave in a first RR interval if it is determined that the first RR interval is greater than or equal to a second RR interval threshold; obtaining peak position information of the at least one new R wave, and then storing peak position information of any new R wave if it is determined that an amplitude of the new R wave is greater than or equal to a second R wave amplitude threshold.

16 Claims, 11 Drawing Sheets

(51) Int. Cl.
*A61B 5/333* (2021.01)
*A61B 5/366* (2021.01)

(58) Field of Classification Search
CPC ..... A61B 5/04012; A61B 5/0402; A61B 5/72; A61B 5/7225; A61B 5/7235; A61B 5/7271
See application file for complete search history.

(56) References Cited

U.S. PATENT DOCUMENTS

| | | | | |
|---|---|---|---|---|
| 2004/0186388 A1* | 9/2004 | Gerasimov | .......... | A61B 5/0456 600/519 |
| 2008/0275516 A1* | 11/2008 | Ghanem | ................ | A61B 5/046 607/9 |
| 2014/0088450 A1* | 3/2014 | Mottaiyan | ............ | A61B 5/0456 600/521 |
| 2014/0128758 A1* | 5/2014 | Galloway | ............ | A61B 5/0472 600/518 |
| 2015/0297907 A1* | 10/2015 | Zhang | ................ | A61N 1/3962 607/7 |
| 2016/0089047 A1* | 3/2016 | Jonnada | ............... | A61B 5/6801 600/516 |
| 2016/0120431 A1* | 5/2016 | Habte | ................. | A61B 5/0428 600/516 |
| 2016/0213275 A1* | 7/2016 | Cao | ........................ | A61B 5/686 |
| 2017/0035363 A1* | 2/2017 | Yoshida | ............... | A61B 5/7203 |
| 2017/0319088 A1* | 11/2017 | George | ............. | A61B 5/04085 |
| 2019/0336026 A1* | 11/2019 | Dawoud | ............. | A61N 1/3756 |

FOREIGN PATENT DOCUMENTS

| | | | |
|---|---|---|---|
| CN | 106974617 A | | 7/2017 |
| CN | 107495959 A | | 12/2017 |
| CN | 107788969 A | | 3/2018 |
| JP | 2003000561 A | | 1/2003 |
| KR | 20120033411 A | * | 4/2012 |
| KR | 20140087918 A | * | 7/2014 |

OTHER PUBLICATIONS

First Office Action issued in corresponding Chinese Application No. 201810543088.X, dated Aug. 28, 2020, with English language translation.

Second Office Action dated Mar. 3, 2021 in Chinese Application No. 201810543088.X, with English translation.

* cited by examiner

METHOD AND APPARATUS FOR PROCESSING ECG SIGNALS, AND ECG MACHINE

CROSS-REFERENCE TO RELATED APPLICATION

This application claims priority to Chinese Patent Application No. 201810543088.X, filed on May 30, 2018, titled "A METHOD AND APPARATUS FOR PROCESSING ECG SIGNALS", which is incorporated herein by reference in its entirety.

TECHNICAL FIELD

The present disclosure relates to the field of electrocardiogram (ECG) signal detection, and in particular, to a method and an apparatus for processing ECG signals, and an ECG machine.

BACKGROUND

Heart disease is one of the major diseases that threaten human life. For a long time, research on heart disease has been an important topic in the medical field. Electrocardiogram (ECG), as a comprehensive manifestation of electrical activity within the heart on the surface of the body, contains abundant physiological and pathological information reflecting the heart rhythm and the electrical conduction. To a certain extent, ECG can objectively reflect the physiological condition of various parts of the heart, and is one of the important bases for diagnosing heart disease and evaluating cardiac function.

SUMMARY

In a first aspect, a method for processing electrocardiogram (ECG) signals is provided. The method includes: removing peak position information of any R wave of a plurality of R waves in a plurality of ECG signals if it is determined according to peak position information of the plurality of R waves that a first RR interval between the R wave and another R wave immediately thereafter is less than or equal to a first RR interval threshold, and an amplitude of the R wave is less than or equal to a first R wave amplitude threshold; storing peak position information of remaining R waves that is not removed; and detecting at least one new R wave in a first RR interval between any R wave of the plurality of R waves in the plurality of ECG signals and another R wave immediately thereafter if it is determined according to the peak position information of the plurality of R waves that the first RR interval is greater than or equal to a second RR interval threshold; obtaining peak position information of the at least one new R wave in the first RR interval, and then storing the peak position information of any new R wave of the at least one new R wave obtained in the first RR interval if it is determined that an amplitude of the new R wave of the at least one new R wave is greater than or equal to a second R wave amplitude threshold.

In some embodiments, the method further includes: denoising the plurality of ECG signals to obtain denoised ECG signals; and obtaining peak position information of the plurality of R waves according to the denoised ECG signals.

In some embodiments, the step of obtaining peak position information of the plurality of R waves, includes: decomposing the denoised ECG signals into components that appear at N scales using a quadratic spline wavelet, wherein N is greater than or equal to 4; obtaining at pairs of positive maximum and negative maximum at a scale $2^j$, wherein the scale $2^j$ is a scale where energy of a QRS complex is concentrated, and j is greater than 1 and less than N; converting data of all pairs of positive maximum and negative maximum at the scale 2 into a first matrix with a fixed time length; selecting at least one pair of positive maximum and negative maximum, in which a positive maximum is greater than or equal to a first preset value and a negative maximum is less than or equal to a second preset value, from each row of the first matrix; and obtaining peak position information of a R wave according to a zero-crossing position and a time shift between a positive maximum and a negative maximum in each selected pair of positive maximum and negative maximum, wherein the time shift is $$\frac{2^j - 1}{2}.$$

On this basis, in some embodiments, each row of the first matrix corresponds to a set of first preset value and second preset value; a first preset value corresponding to an i-th row is $$A(i) = k0 \times \frac{Ai_{max1} + Ai_{max2}}{2},$$

a second preset value corresponding to the i-th row is $$B(i) = k0 \times \frac{Bi_{min1} + Bi_{min2}}{2},$$

wherein i is a row number of the first matrix; $Ai_{max1}$ is the largest value in data at and before a $$\frac{M1}{2}\text{-}th$$

second in the i-th row, $Ai_{max2}$ is the largest value in data after the $$\frac{M1}{2}\text{-}th$$

second in the i-th row, $Bi_{min1}$ is the smallest value in data at and before the $$\frac{M1}{2}\text{-}th$$

second in the i-th row, and $Bi_{min2}$ is the smallest value after the $$\frac{M1}{2}\text{-}th$$

second in the i-th row; wherein k0 is a scale factor less than 1, and M1 is a time length of each row of data.

In some embodiments, the step of removing peak position information of any R wave of a plurality of R waves in a plurality of ECG signals if it is determined according to peak position information of the plurality of R waves that a first RR interval between the R wave and another R wave immediately thereafter is less than or equal to a first RR interval threshold, and an amplitude of the R wave is less than or equal to a first R wave amplitude threshold, includes: converting data of the denoised ECG signals into a second matrix with a fixed time length; calculating an RR interval mean value $RR(p)_{mean}$ of each row in the second matrix and an amplitude mean value $Rh(p)$ of each row in the second matrix according to the peak position information of the plurality of R waves, wherein p is a row number of the second matrix; setting a product of k1 and $RR(p)_{mean}$ as a first RR interval threshold of the p-th row and a product of k2 and $Rh(p)$ as a first R wave amplitude threshold of the p-th row, wherein k1 and k2 are both scale factors less than 1; and removing peak position information of any R wave of R waves in the p-th row if it is determined according to peak position information of the R waves in the p-th row that a first RR interval between the R wave and another R wave immediately thereafter is less than or equal to the first RR interval threshold of the p-th row, and an amplitude of the R wave is less than or equal to the first R wave amplitude threshold of the p-th row.

In some embodiments, the step of removing at least one new R wave in a first RR interval between any R wave of the plurality of R waves in the plurality of ECG signals and another R wave immediately thereafter if it is determined according to the peak position information of the plurality of R waves that the first RR interval is greater than or equal to a second RR interval threshold, includes: setting a product of k3 and $RR(P)_{mean}$ as a second RR interval threshold of the p-th row, wherein k3 is a scale factor greater than 1; obtaining at least one pair of positive maximum and negative maximum, in which a positive maximum is greater than or equal to a third preset value and a negative maximum is less than or equal to a fourth preset value, in a first RR interval between any R wave of the R waves in the p-th row and another R wave immediately thereafter if it is determined according to the peak position information of the R waves in the p-th row that the first RR interval is greater than or equal to the second RR interval threshold of the p-th row, so as to obtain peak position information of the at least one new R wave, wherein the third preset value is less than the first preset value, and an absolute value of the fourth preset value is less than an absolute value of the second preset value.

In some embodiments, the step of obtaining peak position information of the at least one new R wave in the first RR interval, and then storing the peak position information of any new R wave of the at least one new R wave obtained in the first RR interval if it is determined that an amplitude of the new R wave of the at least one new R wave is greater than or equal to a second R wave amplitude threshold, includes: setting a product of k4 and $Rh(p)$ as a second R wave amplitude threshold of the p-th row, wherein k4 is a scale factor less than 1; obtaining peak position information of the at least one new R wave in the first RR interval in the p-th row, and then storing peak position information of any new R wave of the at least one new R wave obtained in the first RR interval if it is determined that an amplitude of the new R wave of the at least one new R wave is greater than or equal to the second R wave amplitude threshold of the p-th row.

In some embodiments, the method further includes: obtaining a start position of a corresponding Q wave and an end position of a corresponding S wave according to the stored peak position information of each R wave.

In some embodiments, the step of obtaining a start position of a corresponding Q wave and an end position of a corresponding S wave according to the stored peak position information of each R wave, includes: setting a peak position of each R wave as a reference point, and setting a first scanning range on a side before a peak of the R wave and a second scanning range on a side after the peak of the R wave; obtaining, in the first scanning range, the number of first inflection points W1 at a scale where energies of a Q wave and an S wave are concentrated; selecting a position of a third first inflection point as the start position of the Q wave if the number of first inflection points W1 is greater than or equal to 3; selecting a position of a first inflection point farthest from the peak of the R wave in the first scanning range as the start position of the Q wave if the number of first inflection points W1 is equal to 1 or 2; selecting a position farthest from the peak of the R wave in the first scanning range as the start position of the Q wave if the number of first inflection points W1 is equal to 0; obtaining the number of second inflection points W2 in the second scanning range; selecting a position of a third second inflection point as the end position of the S wave if the number of second inflection points W2 is greater than or equal to 3; selecting a position of a second inflection point farthest from the peak of the R wave in the second scanning range as the end position of the S wave if the number of second inflection points W2 is equal to 1 or 2; and selecting a position farthest from the peak of the R wave in the second scanning range as the end position of the S wave if the number of second inflection points W2 is equal to 0.

In some embodiments, the step of denoising the plurality of ECG signals, includes: performing wavelet decomposition on the plurality of ECG signals; using a filtering method of thresholding processing to remove a high frequency noise in the plurality of ECG signals; using a zeroing method to remove low frequency baseline drift in the plurality of ECG signals; reconstructing the ECG signals to obtain denoised ECG signals.

In a second aspect, an apparatus for processing ECG signals is provided. The apparatus includes a receiver, a processor and at least one memory. The receiver is configured to receive a plurality of ECG signals recorded by a recorder. The processor is configured to: remove peak position information of any R wave of a plurality of R waves in a plurality of ECG signals if it is determined according to peak position information of the plurality of R waves that a first RR interval between the R wave and another R wave immediately thereafter is less than or equal to a first RR interval threshold, and an amplitude of the R wave is less than or equal to a first R wave amplitude threshold; store peak position information of remaining R waves that is not removed in the at least one memory; and detect at least one new R wave in a first RR interval between any R wave of the plurality of R waves in the plurality of ECG signals and another R wave immediately thereafter if it is determined according to the peak position information of the plurality of R waves that the first RR interval is greater than or equal to a second RR interval threshold; obtain peak position information of the at least one new R wave in the first RR interval, and then store the peak position information of any new R wave of the at least one new R wave obtained in the first RR interval in the at least one memory if it is determined that an amplitude of the new R wave of the at least one new R wave is greater than or equal to a second R wave amplitude threshold.

In some embodiments, the processor is further configured to denoise the plurality of ECG signals to obtain denoised ECG signals; and obtain peak position information of the plurality of R waves according to the denoised ECG signals.

In some embodiments, the processor is further configured to: decompose the denoised ECG signals into components that appear at N scales by using a quadratic spline wavelet, wherein N is greater than or equal to 4; obtain pairs of positive maximum and negative maximum at a scale $2^j$, wherein the scale $2^j$ is a scale where energy of a QRS complex is concentrated, and j is greater than 1 and less than N; convert data of all pairs of positive maximum and negative maximum at the scale $2^j$ into a first matrix with a fixed time length; select at least one pair of positive maximum and negative maximum, in which a positive maximum is greater than or equal to a first preset value and a negative maximum is less than or equal to a second preset value, from each row of the first matrix; and obtain peak position information of a R wave according to a zero-crossing position and a time shift between a positive maximum and a negative maximum in each selected pair of positive maximum and negative maximum, wherein the time shift is $$\frac{2^j - 1}{2}.$$

On this basis, in some embodiments, each row of the first matrix corresponds to a set of first preset value and second preset value; a first preset value corresponding to an i-th row is $$A(i) = k0 \times \frac{Ai_{max1} + Ai_{max2}}{2},$$

a second preset value corresponding to the i-th row is $$B(i) = k0 \times \frac{Bi_{min1} + Bi_{min2}}{2};$$

wherein i is a row number of the first matrix; $Ai_{max1}$ is the largest value in data at and before a $$\frac{M1}{2}\text{-}th$$

second in the i-th row, $Ai_{max2}$ is the largest value in data after the $$\frac{M1}{2}\text{-}th$$

second in the i-th row, $Bi_{min1}$ is the smallest value in data at and before the $$\frac{M1}{2}\text{-}th$$

second in the i-th row, and $Bi_{min2}$ is the smallest value after the $$\frac{M1}{2}\text{-}th$$

second in the i-th row, wherein k0 is a scale factor less than 1, and M1 is a time length of each row of data.

In some embodiments, the processor is further configured to: convert data of the set of denoised ECG signals into a second matrix with a fixed time length; calculate an RR interval mean value $RR(p)_{mean}$ of each row in the second matrix and an amplitude mean value $Rh(p)$ of each row in the second matrix according to the peak position information of the plurality of R waves, wherein p is a row number of the second matrix; set a product of k1 and $RR(p)_{mean}$ as a first RR interval threshold of the p-th row and a product of k2 and $Rh(p)$ as a first R wave amplitude threshold of the p-th row, wherein k1 and k2 are both scale factors less than 1; and remove peak position information of any R wave of R waves in the p-th row if it is determined according to peak position information of the R waves in the p-th row that a first RR interval between the R wave and another R wave immediately thereafter is less than or equal to the first RR interval threshold of the p-th row, and an amplitude of the R wave is less than or equal to the first R wave amplitude threshold of the p-th row.

In some embodiments, the processor is further configured to: set a product of k3 and $RR(p)_{mean}$ as a second RR interval threshold of the p-th row, wherein k3 is a scale factor greater than 1; obtain at least one pair of positive maximum and negative maximum, in which a positive maximum is greater than or equal to a third preset value and a negative maximum is less than or equal to a fourth preset value, in a first RR interval between any R wave of the R waves in the p-th row and another R wave immediately thereafter if it is determined according to the peak position information of the R waves in the p-th row that the first RR interval is greater than or equal to the second RR interval threshold of the p-th row, so as to obtain peak position information of the at least one new R wave, wherein the third preset value is less than the first preset value, and an absolute value of the fourth preset value is less than an absolute value of the second preset value; set a product of k4 and $Rh(p)$ as a second R wave amplitude threshold of the p-th row, wherein k4 is a scale factor less than 1; obtain peak position information of the at least one new R wave in the first RR interval in the p-th row, and then store peak position information of any new R wave of the at least one new R wave obtained in the first RR interval in the at least one memory if it is determined that an amplitude of the new R wave of the at least one new R wave is greater than or equal to the second R wave amplitude threshold of the p-th row.

In some embodiments, the processor is further configured to obtain a start position of a corresponding Q wave and an end position of a corresponding S wave according to the stored peak position information of each R wave.

In a third aspect, a non-transitory computer-readable storage medium is provided, and the medium stores executable instructions that, when executed by an electrocardiogram device, cause the electrocardiogram device to implement the method according to the first aspect.

In a fourth aspect, an ECG machine is provided. The ECG machine includes a recorder and the apparatus for processing ECG signals according to the second aspect. The recorder is configured to record a plurality of ECG signals. The apparatus for processing ECG signals is configured to process the plurality of ECG signals.

BRIEF DESCRIPTION OF THE DRAWINGS

In order to describe technical solutions in embodiments in the present disclosure more clearly, the accompanying drawings to be used in the description of embodiments will be introduced briefly. Obviously, the accompanying drawings to be described below are merely some embodiments of the present disclosure, and a person of ordinary skill in the art can obtain other drawings according to these drawings without paying any creative effort.

DETAILED DESCRIPTION

The technical solutions in the embodiments of the present disclosure will be described clearly and completely with reference to the accompanying drawings in the embodiments of the present disclosure. Obviously, the described embodiments are merely some but not all of embodiments of the present disclosure. All other embodiments made on the basis of the embodiments of the present disclosure by a person of ordinary skill in the art without paying any creative effort shall be included in the protection scope of the present disclosure.

Figure 3:
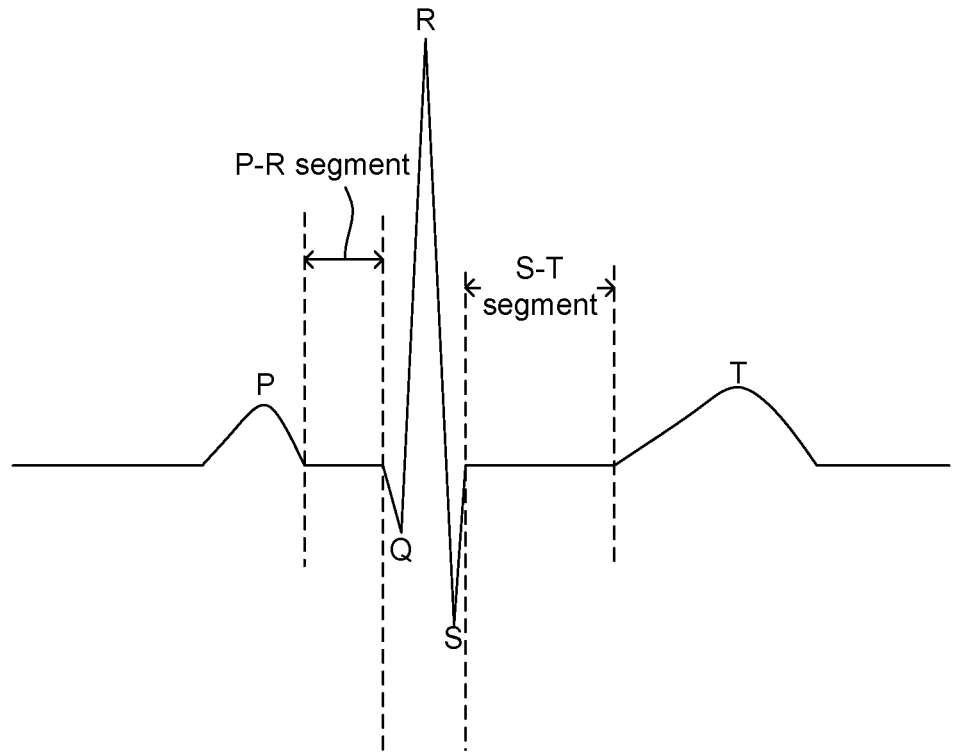
FIG. 3 is a schematic diagram of an ECG signal, in accordance to some embodiments.

An electrocardiogram (ECG) signal is a signal of an ECG voltage (amplitude) measured by body-surface electrodes as a function of time, and is a time domain waveform signal. As shown in FIG. 3, a normal ECG waveform can be divided into several major parts including a P wave, a P-R segment, a QRS complex, a S-T segment, and a T wave. Each characteristic band has a certain physiological significance. If the heart develops a lesion, it will cause some distortion in the cycle and waveform morphology of the ECG signal.

The frequency of human ECG signals is low. The main frequency range is 0.05~100 Hz, and most of the energy is concentrated in 0.5~45 Hz. The energy of the QRS complex accounts for a large proportion of the energy of the ECG signal, and is distributed in the middle and high frequency regions of the ECG signal. Therefore, the QRS complex is the most recognizable and the most important characteristic band in the ECG signal, while the R wave is the most recognizable band in the QRS complex.

Figure 13:
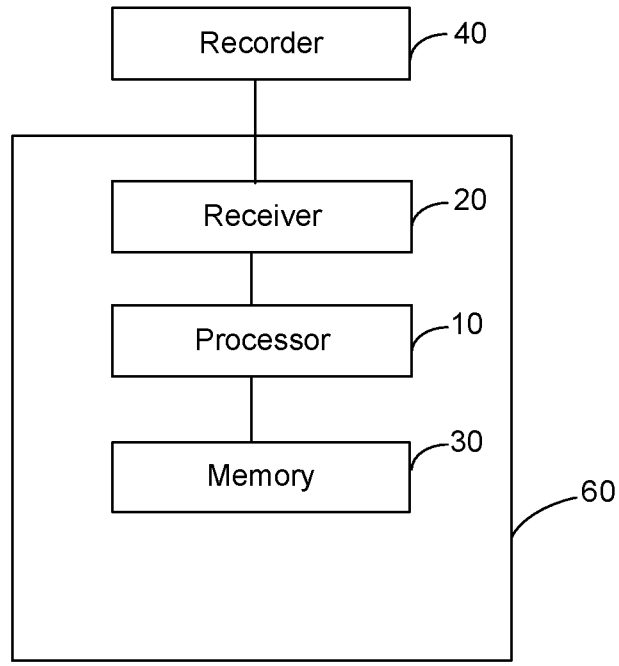
FIG. 13 is a schematic diagram of an apparatus for processing ECG signals, in accordance with some embodiments.

Some embodiments of the present disclosure provide a method for processing ECG signals. The method is performed by, for example, an apparatus for processing ECG signals as shown in FIG. 13. In some examples, the apparatus for processing ECG signals is an ECG machine. The ECG machine includes, for example, a recorder for recording ECG waveforms (ECG signals) and an analysis diagnostic component such as a central processing unit (CPU). In some other examples, the apparatus for processing ECG signals is an analysis diagnostic device connected to an ECG machine that includes a recorder for recording ECG waveforms (ECG signals).

Figure 1:
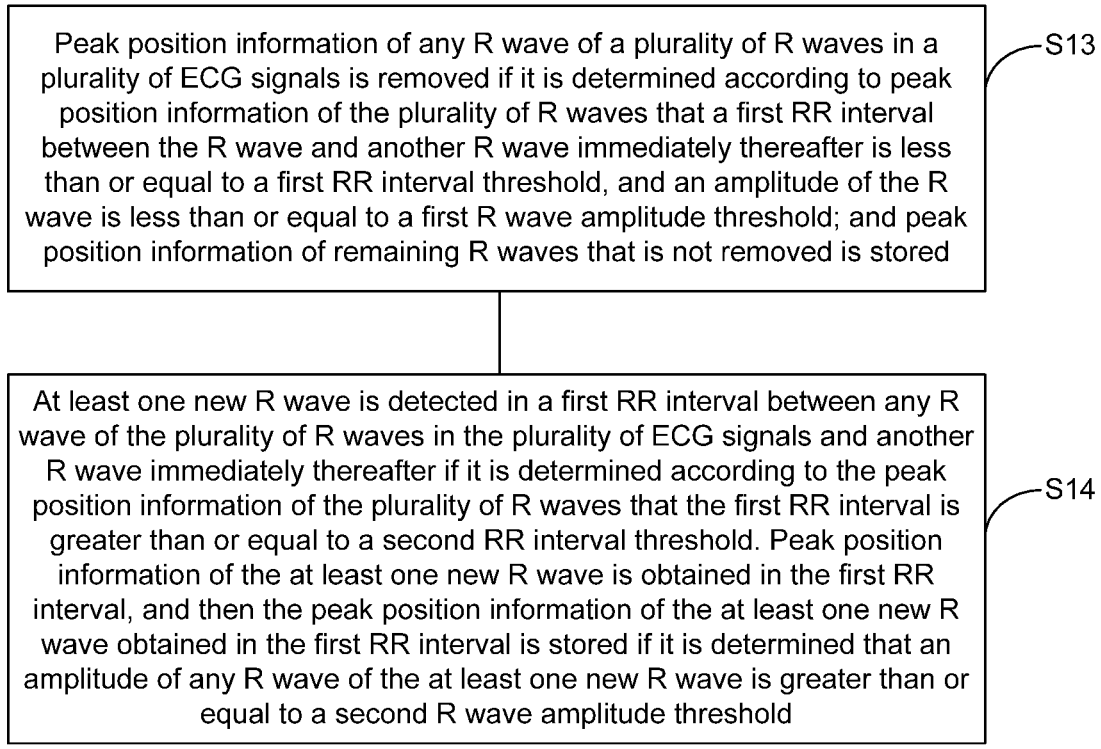
FIG. 1 is a flow chart of a method for processing electrocardiogram (ECG) signals, in accordance with some embodiments.

As shown in FIG. 1, the method for processing ECG signals includes step 13 (S13) and step 14 (S14).

In S13, peak position information of any R wave of a plurality of R waves in a plurality of ECG signals is removed if it is determined according to peak position information of the plurality of R waves that a first RR interval between the R wave and another R wave immediately thereafter is less than or equal to a first RR interval threshold, and an amplitude of the R wave is less than or equal to a first R wave amplitude threshold; and peak position information of remaining R waves that is not removed is stored.

Herein, "another wave immediately thereafter" refers to a wave which is recorded later in timing with respect to a previously mentioned wave among a plurality of ECG signals recorded in chronological order, and is only used in the method provided in the embodiments of the present disclosure to distinguish between two adjacent waves.

For example, starting from a first R wave, it is first determined whether the first RR interval between the first R wave and a second R wave immediately thereafter is less than or equal to the first RR interval threshold. If yes, then it is determined whether an amplitude of the first R wave is less than or equal to the first R wave amplitude threshold. If the amplitude of the first R wave is less than or equal to the first R wave amplitude threshold, then peak position information of the first R wave is removed. If the first RR interval between the first R wave and the second R wave immediately thereafter is greater than the first RR interval threshold, then it is determined whether a first RR interval between the second R wave and a third R wave immediately thereafter is less than or equal to the first RR interval threshold. If the first RR interval between the second R wave and the third R wave immediately thereafter is also greater than the first RR interval threshold, then it is determined whether a first RR interval between the third R wave and a fourth R wave immediately thereafter is less than or equal to the first RR interval threshold. If the first RR interval between the third R wave and the fourth R wave immediately thereafter is less than or equal to the first RR interval threshold, then it is determined whether an amplitude of the third R wave is less than or equal to the first R wave amplitude threshold. Then, the rest are deduced by analogy: it is first determined whether a first RR interval between a current R wave and another R wave immediately thereafter is less than or equal to the first RR interval threshold, and only in a case where the first RR interval is less than or equal to the first RR interval threshold, it is determined whether an amplitude of the current R wave is less than or equal to the first R wave amplitude threshold. After the determination processes are completed, the peak position information of the remaining R waves that is not removed is stored.

In S14, at least one new R wave is detected in a first RR interval between any R wave of the plurality of R waves in the plurality of ECG signals and another R wave immediately thereafter if it is determined according to the peak position information of the plurality of R waves that the first RR interval is greater than or equal to a second RR interval threshold. Peak position information of the at least one new R wave is obtained, and then the peak position information of any new R wave of the at least one new R wave is stored if it is determined that an amplitude of the new R wave of the at least one new R wave is greater than or equal to a second R wave amplitude threshold.

For example, starting from the first R wave, it is first determined whether a first RR interval between the first R wave and the second R wave immediately thereafter is greater than or equal to a second RR interval threshold. If yes, then at least one new R wave is detected in the first RR interval. The peak position information of the at least one new R wave is obtained, and then it is determined whether an amplitude of any R wave of the at least one new R wave is greater than or equal to the second R wave amplitude threshold. If yes, the peak position information of the new R wave of the at least one new R wave is stored; otherwise, the peak position information of the new R wave of the at least one new R wave is not stored. If the first RR interval between the first R wave and the second R wave immediately thereafter is less than the second RR interval threshold, then it is determined whether a first RR interval between the second R wave and a third R wave immediately thereafter is greater than or equal to the second R interval threshold. If the first RR interval between the second R wave and the third R wave immediately thereafter is also less than the second RR interval threshold, then it is determined whether a first RR interval between the third R wave and a fourth R wave immediately thereafter is greater than or equal to the second R interval threshold. If the first RR interval between the third R wave and the fourth R wave immediately thereafter is greater than or equal to the second RR interval threshold, then at least one new R wave is detected in the first RR interval. The peak position information of the at least one new R wave is obtained, and then it is determined whether an amplitude of any R wave of the at least one new R wave is greater than or equal to the second R wave amplitude threshold. If yes, the peak position information of the new R wave of the at least one new R wave is stored; otherwise, the peak position information of the new R wave of the at least one new R wave is not stored. Then, the rest are deduced by analogy: it is first determined whether a first RR interval between a current R wave and another R wave immediately thereafter is greater than or equal to the second RR interval threshold, and only in a case where the first RR interval is greater than or equal to the second RR interval threshold, at least one new R wave is detected in a corresponding first RR interval, and it is determined whether an amplitude of the any R wave of the at least one new R wave is greater than or equal to the second R wave amplitude threshold.

In the method for processing ECG signals provided by the embodiments of the present disclosure, by determining whether a first RR interval between any two adjacent R waves is less than or equal to the first RR interval threshold and whether an amplitude of the previous one of the two adjacent R waves is less than or equal to a first R wave amplitude threshold according to the peak position information of the plurality of R waves, the peak position information of falsely detected R waves may be removed. Moreover, in a case where a first RR interval between two adjacent R waves is greater than or equal to the second RR interval threshold, at least one new R wave is detected in the first RR interval. Then the peak position information of the at least one new R wave is obtained, and if an amplitude of any new R wave of the at least one new R wave is greater than or equal to the second R wave amplitude threshold, the new R wave of the at least one new R wave will be considered as a missed R wave, and the peak position information of the new R wave will be stored. Based on this, compared with one-time R wave positioning of the conventional method, which usually neglects false detection or missed detection of peak positions of R waves due to poor signal quality or abnormal heartbeat and thereby causes heart rate distortion and arrhythmia, the technical solution provided by some embodiments of the present disclosure may improve a correct detection rate of R waves in the ECG signals, and make up for the deficiency of false detection and missed detection in the detection process of the QRS complex in ECG signals. For example, the correct detection rate of R waves in ECG signals of the ECG machine may be improved.

In some embodiments, ECG signals are obtained by recording by a recorder, or are obtained through a preliminary processing or conversion process after they are recorded by the recorder. Then the ECG signals are stored in at least one memory.

Figure 2:
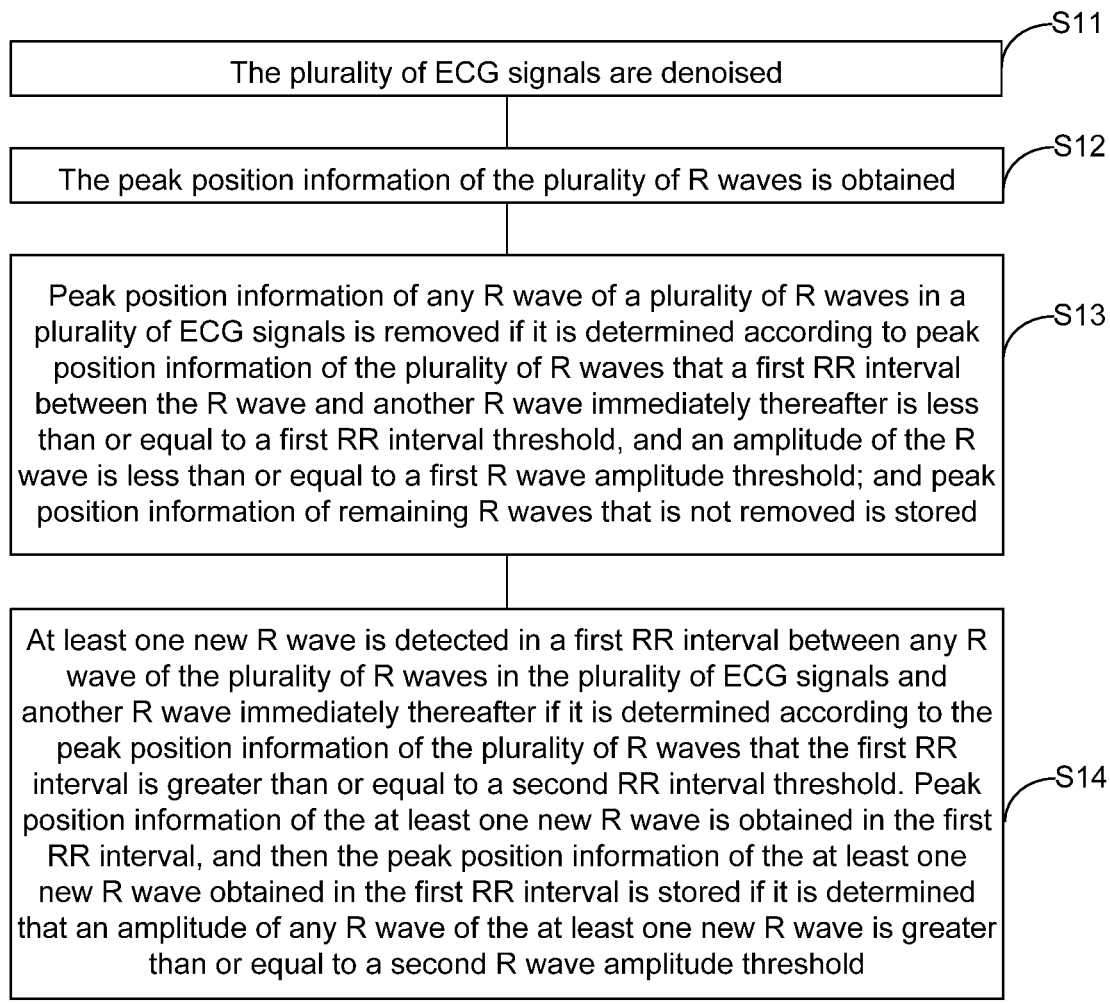
FIG. 2 is a flow chart of another method for processing ECG signals, in accordance with some embodiments.

In some embodiments, as shown in FIG. 2, the method further includes step 11 (S11) and step 12 (S12).

In S11, the plurality of ECG signals are denoised.

In S12, the peak position information of the plurality of R waves is obtained.

The peak position information of the plurality of R waves used in S13 and S14 is obtained in S12. In addition, by denoising the plurality of ECG signals, a signal-to-noise ratio may be improved.

Figure 4:
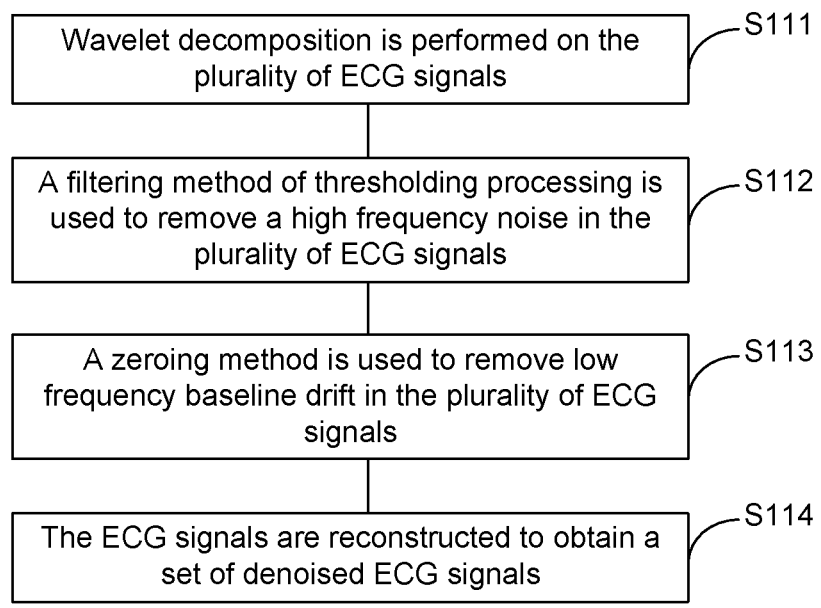
FIG. 4 is a flow chart of a method for denoising ECG signals, in accordance with some embodiments.

In some embodiments, as shown in FIG. 4, the step of denoising the plurality of ECG signals in S11 includes step 111 to step 114 (S111 to S114).

In S111, wavelet decomposition is performed on the plurality of ECG signals.

In some embodiments, the plurality of ECG signals are decomposed into 8-12 layers by wavelet decomposition. For example, the plurality of ECG signals are decomposed into 10 layers.

In S112, a filtering method of thresholding processing is used to remove a high frequency noise in the plurality of ECG signals.

For example, wavelet detail coefficients corresponding to the high-frequency noise are denoised by soft-threshold denoising, so as to remove the high-frequency noise.

As known by a person skilled in the art, frequency bands of useful signals in ECG signals are generally concentrated in 0.5~45 Hz, and frequency bands above 45 Hz are all referred to as high-frequency noise.

In S113, low frequency baseline drift is removed from the ECG signal by using a zeroing method.

Wavelet detail coefficients corresponding to the low frequency baseline drift may be zeroed, so as to remove the low frequency baseline drift.

The baseline drift is caused by breathing, and a frequency range of the baseline drift is 0.05~2 Hz.

In S114, the ECG signals are reconstructed to obtain denoised ECG signals.

In the above embodiments, after the noisy signal is decomposed into a number of scales according to the multi-resolution analysis theory of wavelet transform, detail components corresponding to the noise may be directly removed based on a difference in frequency spectrum and energy distribution between the signal and the noise. Then the ECG signal is reconstructed through inverse wavelet transform, so that the noise in the ECG signal may be effectively removed.

Figure 5:
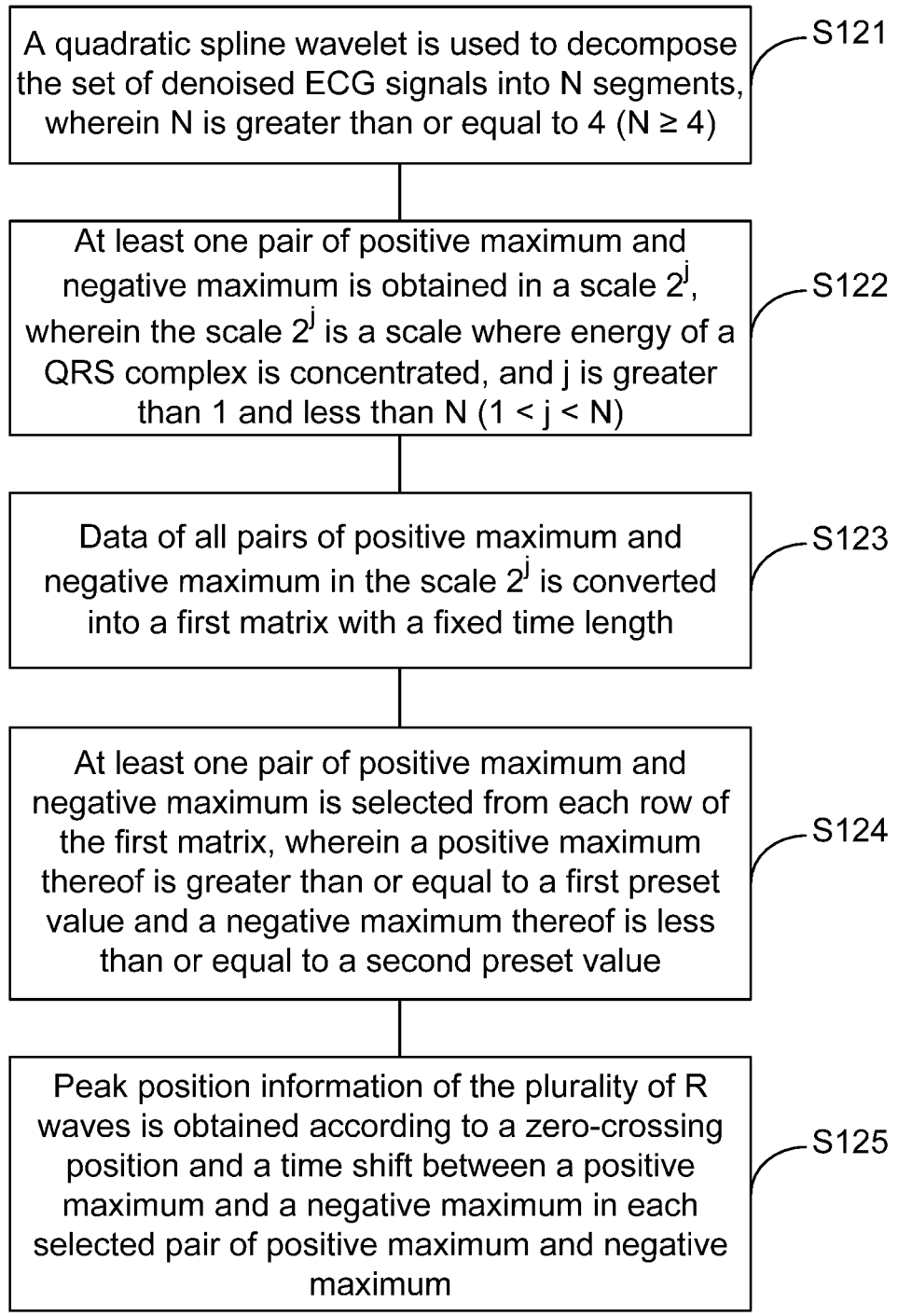
FIG. 5 is a flow chart of a method for obtaining peak position information of an R wave, in accordance with some embodiments.

In some embodiments, as shown in FIG. 5, the step of obtaining the peak position information of the plurality of R waves in S12 includes step 121 to step 125 (S121~S125).

In S121, denoised ECG signals are decomposed into components that appear at N scales by using a quadratic spline wavelet, wherein N is greater than or equal to 4 (N≥4).

In S122, pairs of positive maximum and negative maximum are obtained at a scale $2^j$, wherein the scale $2^j$ is a scale where energy of a QRS complex is concentrated, and j is greater than 1 and less than N (1<j<N).

In S123, data of all pairs of positive maximum and negative maximum in the scale $2^j$ is converted into a first matrix with a fixed time length.

In S124, at least one pair of positive maximum and negative maximum, in which a positive maximum is greater than or equal to a first preset value and a negative maximum is less than or equal to a second preset value, is selected from each row of the first matrix.

In S125, peak position information of a R wave is obtained according to a zero-crossing position and a time shift between a positive maximum and a negative maximum in each selected pair of positive maximum and negative maximum, wherein the time shift is $$\frac{2^j - 1}{2}.$$

In some embodiments, each row of the first matrix corresponds to a set of first preset value and second Preset value. A first preset value corresponding to an i-th row is $$A(i) = k0 \times \frac{Ai_{max1} + Ai_{max2}}{2},$$

a second preset value corresponding to the i-th row is $$B(i) = k0 \times \frac{Bi_{min1} + Bi_{min2}}{2},$$

wherein i is a row number of the first matrix, $Ai_{max1}$ is the largest value in data at and before a $$\frac{M1}{2}\text{-}th$$

second in the i-th row, $Ai_{max2}$ is the largest value in data after the $$\frac{M1}{2}\text{-}th$$

second in the i-th row, $Bi_{min1}$ is the smallest value in data at and before the $$\frac{M1}{2}\text{-}th$$

second in the i-th row, and $Bi_{min2}$ is the smallest value after the $$\frac{M1}{2}\text{-}th$$

second in the i-th row, k0 is a scale factor less than 1, and M1 is a time length of each row of data. In some embodiments, M1 is a even number. Herein "before" refers to a relative sequential relationship of the data in chronological order.

For example, N is equal to 4 (N=4). In this case, energy of the QRS complex is most concentrated at a scale $2^3$. Based on this, pairs of positive maximum and negative maximum are obtained at the scale $2^3$. After all pairs of positive maximum and negative maximum are obtained at the scale $2^3$, data of all pairs of positive maximum and negative maximum is converted into a first matrix with a fixed time length of 10 seconds (i.e., M1=10).

A first preset value and a second preset value are set for each row of the first matrix. The i-th row corresponds to the first preset value A(i) and the second preset value B(i), wherein $$A(i) = k0 \times \frac{Ai_{max1} + Ai_{max2}}{2}, B(i) = k0 \times \frac{Bi_{min1} + Bi_{min2}}{2},$$

and i is a row number of the first matrix. Since M1=10, $Ai_{max1}$ is the largest value in data at and before a 5th second in the i-th row, $Ai_{max2}$ is the largest value in data after the 5th second in the i-th row, $Bi_{min1}$ is the smallest value in data at and before the 5th second in the i-th row, and $Bi_{min2}$ is the smallest value after the 5th second in the i-th row. k0 may be set to a value from ¼ to ⅖. For example, k0 is set to ⅓.

Based on this, at least one pair of positive maximum and negative maximum, in which a positive maximum is greater than or equal to A(i) and a negative maximum is less than or equal to B(i), is selected from each row of the first matrix. In addition, peak position information of a R wave is obtained according to a zero-crossing position and a time shift between a positive maximum and a negative maximum in each of the at least one pair of positive maximum and negative maximum, and then recorded.

It will be noted that, in a case where multiscale decomposition of the denoised ECG signals are performed by using the quadratic spline wavelet, the denoised ECG signals may be decomposed into components that appear at 5 scales or 6 scales. In a case where the number of scales is changed, that is, N is changed, j is changed.

In the above embodiments of the present disclosure, by obtaining pairs of positive maximum and negative maximum at the scale $2^j$ and then converting data of all pairs of positive maximum and negative maximum into a first matrix with a fixed time length, a small segment of data may be processed at a time, thereby avoiding accumulation of errors.

Figure 6:
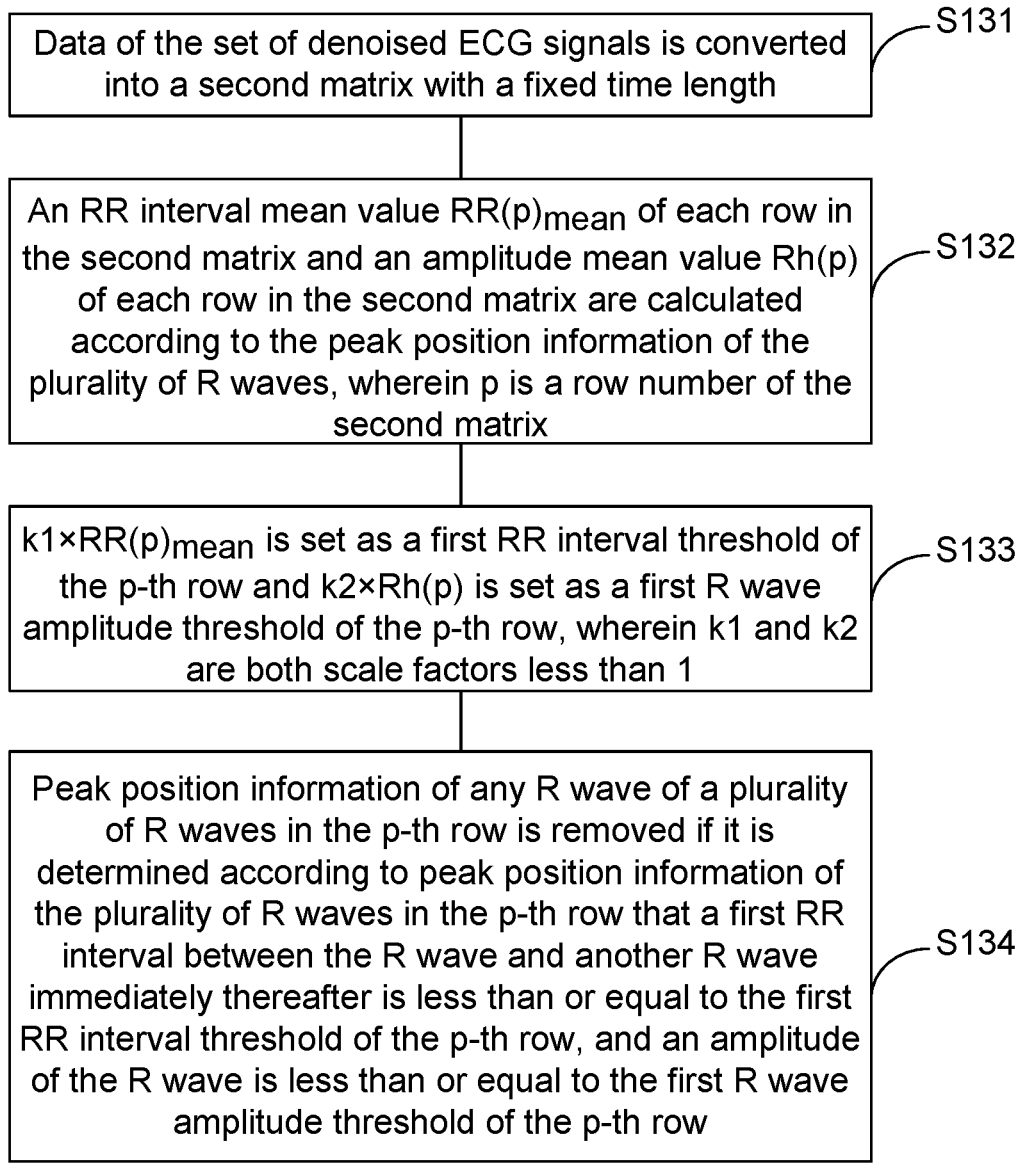
FIG. 6 is a flow chart of a method for removing non-compliant R waves, in accordance with some embodiments.

In some embodiments, as shown in FIG. 6, the step of removing peak position information of any R wave of a plurality of R waves in a plurality of ECG signals if it is determined according to peak position information of the plurality of R waves that a first RR interval between the R wave and another R wave immediately thereafter is less than or equal to a first RR interval threshold, and an amplitude of the R wave is less than or equal to a first R wave amplitude threshold in S13 includes step 131 to step 134 (S131-S134).

In S131, data of the denoised ECG signals is converted into a second matrix with a fixed time length.

In S132, an RR interval mean value $RR(p)_{mean}$ of each row in the second matrix and an amplitude mean value $Rh(p)$ of each row in the second matrix are calculated according to the peak position information of the plurality of R waves, wherein p is a row number of the second matrix.

That is, an RR interval mean value of the first row is $RR(1)_{mean}$, and an amplitude mean value of the first row is $Rh(1)$. An RR interval mean value of the second row is $RR(2)_{mean}$, and an amplitude mean value of the second row is $Rh(2)$. An RR interval mean value of the fifth row is $RR(5)_{mean}$, and an amplitude mean value of the fifth row is $Rh(5)$. An RR interval mean value of the tenth row is $RR(10)_{mean}$ and an amplitude mean value of the tenth row is $Rh(10)$.

In S133, a product of k1 and) $RR(p)_{mean}$ (k1×$RR(p)_{mean}$) is set as a first RR interval threshold of the p-th row and a product of k2 and $Rh(p)$ (k2×$Rh(p)$) is set as a first R wave amplitude threshold of the p-th row, wherein k1 and k2 are both scale factors less than 1.

In some embodiments, k1 is equal to k2. k1 and k2 may be set to values from ¼ to ⅖. For example, k1 and k2 are both set to 1.

A first RR interval threshold of the first row is k1×RR(1) mean, and a first R wave amplitude threshold of the first row is k2×Rh(1). A first RR interval threshold of the second row is k1×$RR(2)_{mean}$, and a first R wave amplitude threshold of the second row is k2×Rh(2). A first RR interval threshold of the fifth row is k1×$RR(5)_{mean}$, and a first R wave amplitude threshold of the fifth row is k2×Rh(5). A first RR interval threshold of the tenth row is k1×$RR(10)_{mean}$, and a first R wave amplitude threshold of the tenth row is k2×Rh(10).

In S134, peak position information of any R wave of R waves in the p-th row is removed if it is determined according to peak position information of the R waves in the p-th row that a first RR interval between the R wave and another R wave immediately thereafter is less than or equal to the first RR interval threshold of the p-th row, and an amplitude of the R wave is less than or equal to the first R wave amplitude threshold of the p-th row.

As known by a person skilled in the art, there is no RR interval for a last R wave in each row. Therefore, in an actual design process, it is not necessary to determine whether an amplitude of the last R wave is less than or equal to the first R wave amplitude. That is, peak position information of the last R wave of each row is necessarily retained.

It will be noted that, in the above embodiments, the first RR interval threshold and the first R wave amplitude threshold of each row adopt fixed ratios respectively. In some other embodiments, the first RR interval threshold and the first R wave amplitude threshold of each row may also be dynamically adjusted adaptively.

Figure 7:
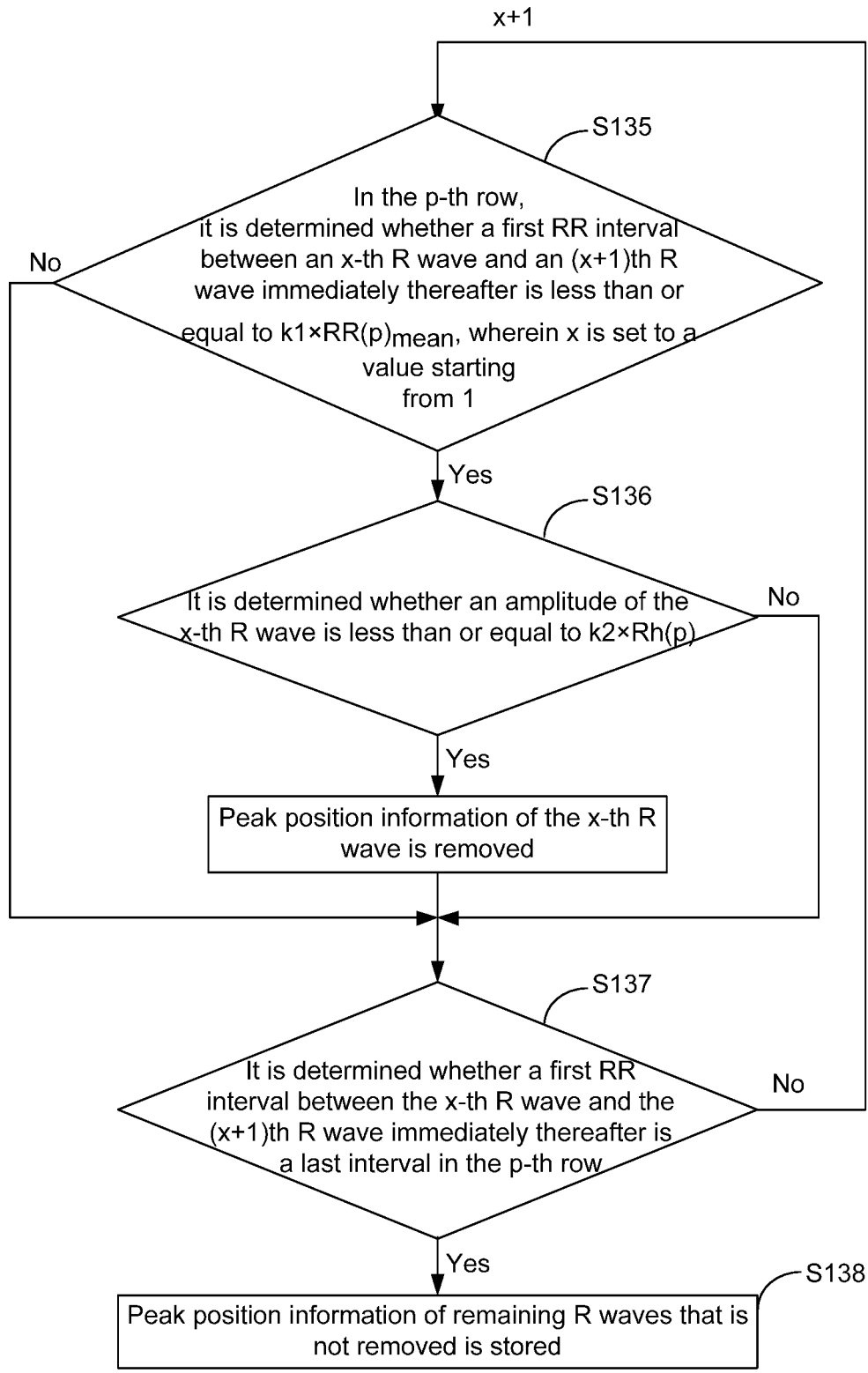
FIG. 7 is a flow chart of another method for removing non-compliant R waves, in accordance with some embodiments.

In some embodiments, for any row of the second matrix (such as the p-th row), the step of removing peak position information of any R wave of the R waves in the p-th row if it is determined according to peak position information of R waves in the p-th row that a first RR interval between the R wave and another R wave immediately thereafter is less than or equal to the first RR interval threshold of the p-th row, and an amplitude of the R wave is less than or equal to the first R wave amplitude threshold of the p-th row may be implemented through step 135 to step 138 (S135 to S138), as shown in FIG. 7.

In S135, in the p-th row, whether a first RR interval between an x-th R wave and an (x+1)th R wave immediately thereafter is less than or equal to k1×$RR(p)_{mean}$ is determined, wherein x is set to a value starting from 1. If yes, then S136 is executed; otherwise, S137 is executed.

In S136, whether an amplitude of the x-th R wave is less than or equal to k2×Rh(p) is determined. If yes, then peak position information of the x-th R wave is removed; otherwise, S137 is executed.

In S137, whether a first RR interval between the x-th R wave and the (x+1)th R wave immediately thereafter is a last interval in the p-th row is determined. If yes, then S138 is executed; otherwise, 1 is added to x, and S135 is executed.

In S138, peak position information of remaining R waves that is not removed is stored.

Figure 8:
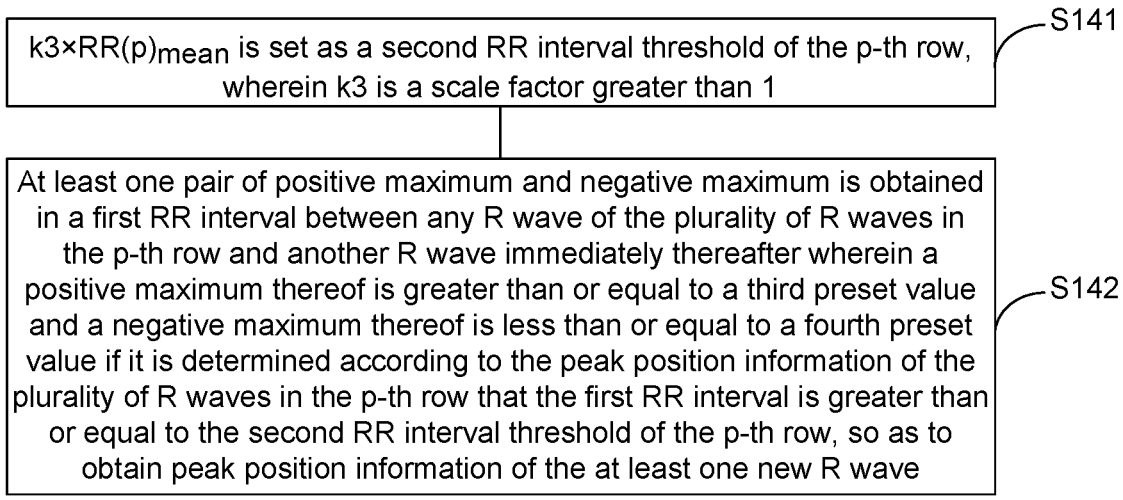
FIG. 8 is a flow chart of a method for detecting new R waves, in accordance with some embodiments.

In some embodiments, as shown in FIG. 8, the step of detecting at least one new R wave in a first RR interval between any R wave of the plurality of R waves in the plurality of ECG signals and another R wave immediately thereafter if it is determined according to the peak position information of the plurality of R waves that the first RR interval is greater than or equal to a second RR interval threshold in S14 includes step 141 (S141) and step 142 (S142).

In S141, a product of k3 and) $RR(p)_{mean}$ (k3×$RR(P)_{mean}$) is set as a second RR interval threshold of the p-th row, wherein k3 is a scale factor greater than 1.

That is, a second RR interval threshold of the first row is k3×$RR(1)_{mean}$. A second RR interval threshold of the second row is k3×$RR(2)_{mean}$. A second RR interval threshold of the fifth row is k3×$RR(5)_{mean}$. A second RR interval threshold of the tenth row is k3×$RR(10)_{mean}$. k3 may be set to a value from 8/5 to 7/4. For example, k3 is set to 5/3.

In S142, at least one pair of positive maximum and negative maximum, in which a positive maximum is greater than or equal to a third preset value and a negative maximum is less than or equal to a fourth preset value, is detected in a first RR interval between any R wave of the R waves in the p-th row and another R wave immediately thereafter if it is determined according to the peak position information of the R waves in the p-th row that the first RR interval is greater than or equal to the second RR interval threshold of the p-th row, so as to obtain peak position information of the at least one new R wave.

The third preset value is less than the first preset value, and an absolute value of the fourth preset value is less than an absolute value of the second preset value.

Figure 9:
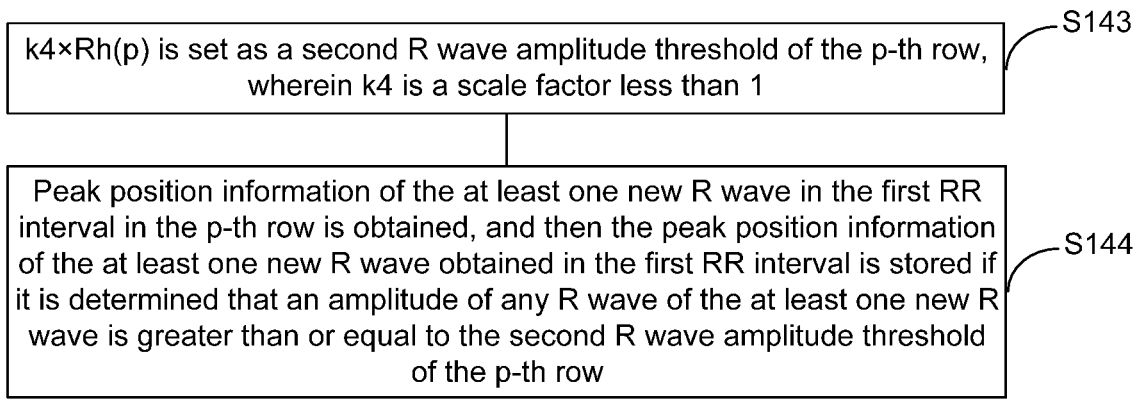
FIG. 9 is a flow chart of a method for determining whether a new R wave is compliant, in accordance with some embodiments.

Based on this, as shown in FIG. 9, the step of obtaining peak position information of the at least one new R wave in the first RR interval, and then storing the peak position information of any new R wave of the at least one new R wave obtained in the first RR interval if it is determined that an amplitude of the new R wave of the at least one new R wave is greater than or equal to a second R wave amplitude threshold in S14 includes step 143 (S143) and step 144 (S144).

In S143, a product of k4 and Rh(p) (k4×Rh(p)) is set as a second R wave amplitude threshold of the p-th row, wherein k4 is a scale factor less than 1.

That is, a second R wave amplitude threshold of the first row is k4×Rh(1). A second R wave amplitude threshold of the second row is k4×Rh(2). A second R wave amplitude threshold of the fifth row is k4×Rh(5). A second R wave amplitude threshold of the tenth row is k4×Rh(10). k4 may be set to a value from ⅗ to ¾. For example, k4 is set to ⅔.

In S144, peak position information of the at least one new R wave in the first RR interval in the p-th row is obtained, and then the peak position information of any new R wave of the at least one new R wave obtained in the first RR interval is stored if it is determined that an amplitude of the new R wave of the at least one new R wave is greater than or equal to the second R wave amplitude threshold of the p-th row.

It will be noted that, S141-S142 and S143-S144 are both implemented with row as a unit in the second matrix.

In addition, in the above embodiments, the second RR interval threshold and the second R wave amplitude threshold of each row adopt fixed ratios respectively. In some other embodiments, the second RR interval threshold and the second R wave amplitude threshold of each row may also be dynamically adjusted adaptively.

Figure 10:
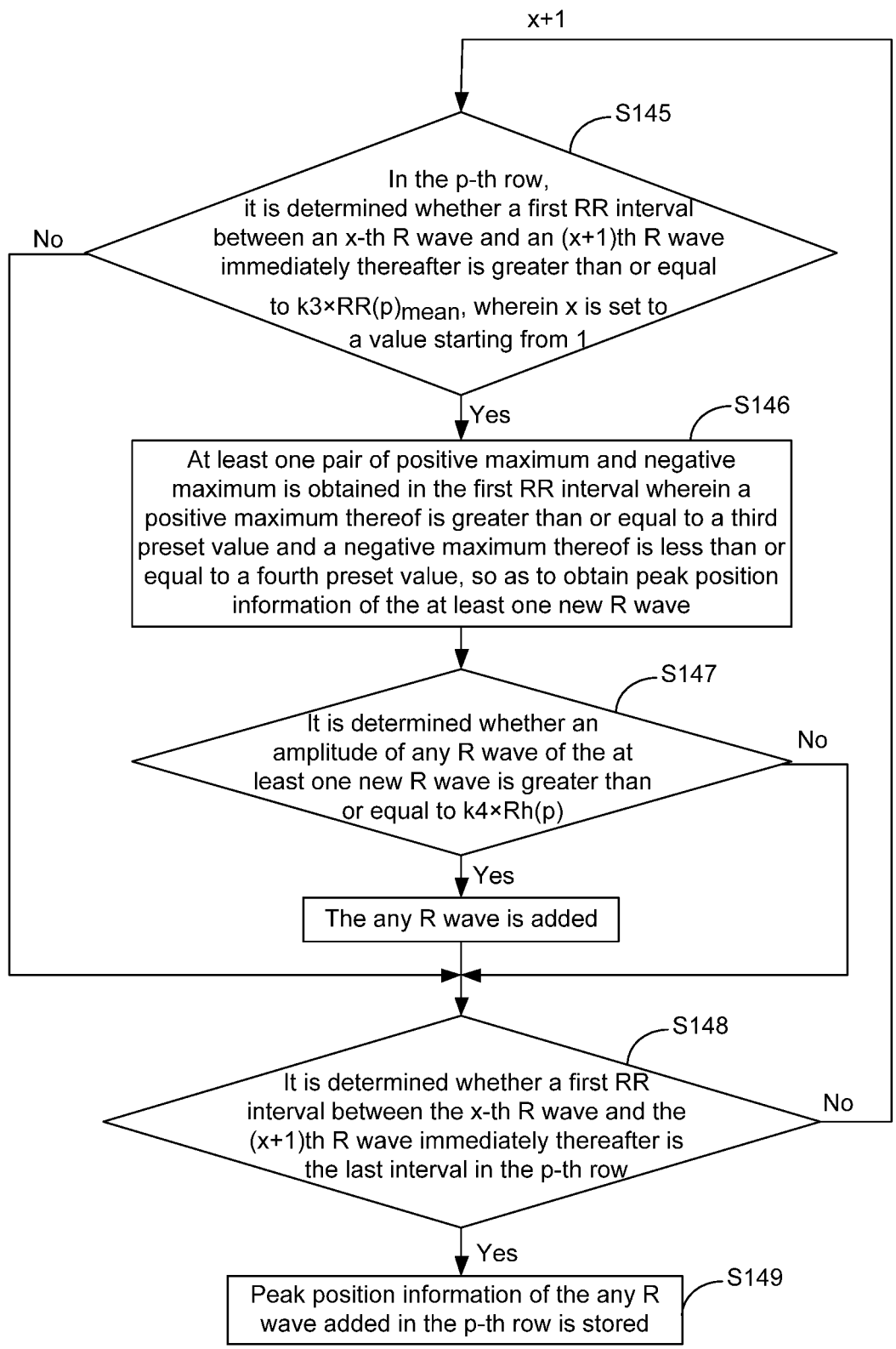
FIG. 10 is a flow chart of a method for adding a R wave, in accordance with some embodiments.

For any row of the second matrix (such as the p-th row), the steps of obtaining at least one pair of positive maximum and negative maximum, in which a positive maximum is greater than or equal to a third preset value and a negative maximum is less than or equal to a fourth preset value, in a first RR interval between any R wave of R waves in the p-th row and another R wave immediately thereafter if it is determined according to the peak position information of the R waves in the p-th row that the first RR interval is greater than or equal to the second RR interval threshold of the p-th row, obtaining peak position information of the at least one new R wave in the first RR interval in the p-th row, and then storing the peak position information of any new R wave of the at least one new R wave obtained in the first RR interval if it is determined that an amplitude of the new R wave of the at least one new R wave is greater than or equal to the second R wave amplitude threshold of the p-th row are implemented through step 145 to step 149 (S145-S149), as shown in FIG. 10.

In S145, in the p-th row, whether a first RR interval between an x-th R wave and an (x+1)th R wave immediately thereafter is greater than or equal to a product of k3 and $RR(p)_{mean}$ (k3×RR(P)$_{mean}$) is determined, wherein x is set to a value starting from 1. If yes, then S146 is executed; otherwise, S148 is executed.

In S146, at least one pair of positive maximum and negative maximum, in which a positive maximum is greater than or equal to a third preset value and a negative maximum is less than or equal to a fourth preset value, is obtained in the first RR interval, so as to obtain peak position information of the at least one new R wave.

The third preset value is less than the first preset value, and an absolute value of the fourth preset value is less than an absolute value of the second preset value.

In a process of obtaining the peak position information of the R waves, after at least one pair of positive maximum and negative maximum is obtained at a scale $2^j$, and data of all pairs of positive maximum and negative maximum at the scale $2^j$ is converted into a first matrix with a fixed time length, since the at least one pair of positive maximum and negative maximum is selected from each row of the first matrix with the first preset value $$A(i) = k0 \times \frac{Ai_{max1} + Ai_{max2}}{2}$$

and the second preset value $$B(i) = k0 \times \frac{Bi_{min1} + Bi_{min2}}{2}$$

as reference values, in this step, the third preset value and the fourth preset value may be obtained by only reducing the value of k0 in calculation formulas of the first preset value and the second preset value. That is, if $$k0 = \frac{D1}{D2},$$

then, a value of (D2+T) is used to replace the value of D2 in k0 in the formula of the first preset value to obtain the third preset value, and a value of (D2+T) is used to replace the value of D2 in k0 in the formula of the second preset value to obtain the fourth preset value. Herein D1, D2, and T are all positive integers. For example, D1 is set to 1, D2 is set to 3, and T is set to 1.

In S147, whether an amplitude of any R wave of the at least one new R wave is greater than or equal to a product of k4 and Rh(p) (k4×Rh(p)) is determined. If yes, the R wave is added; otherwise, S148 is executed.

In S148, whether a first RR interval between the x-th R wave and the (x+1)th R wave immediately thereafter is the last interval in the p-th row is determined. If yes, S149 is executed; otherwise, 1 is added to x, and S145 is executed.

In S149, peak position information of the R wave added in the p-th row is stored.

Figure 11:
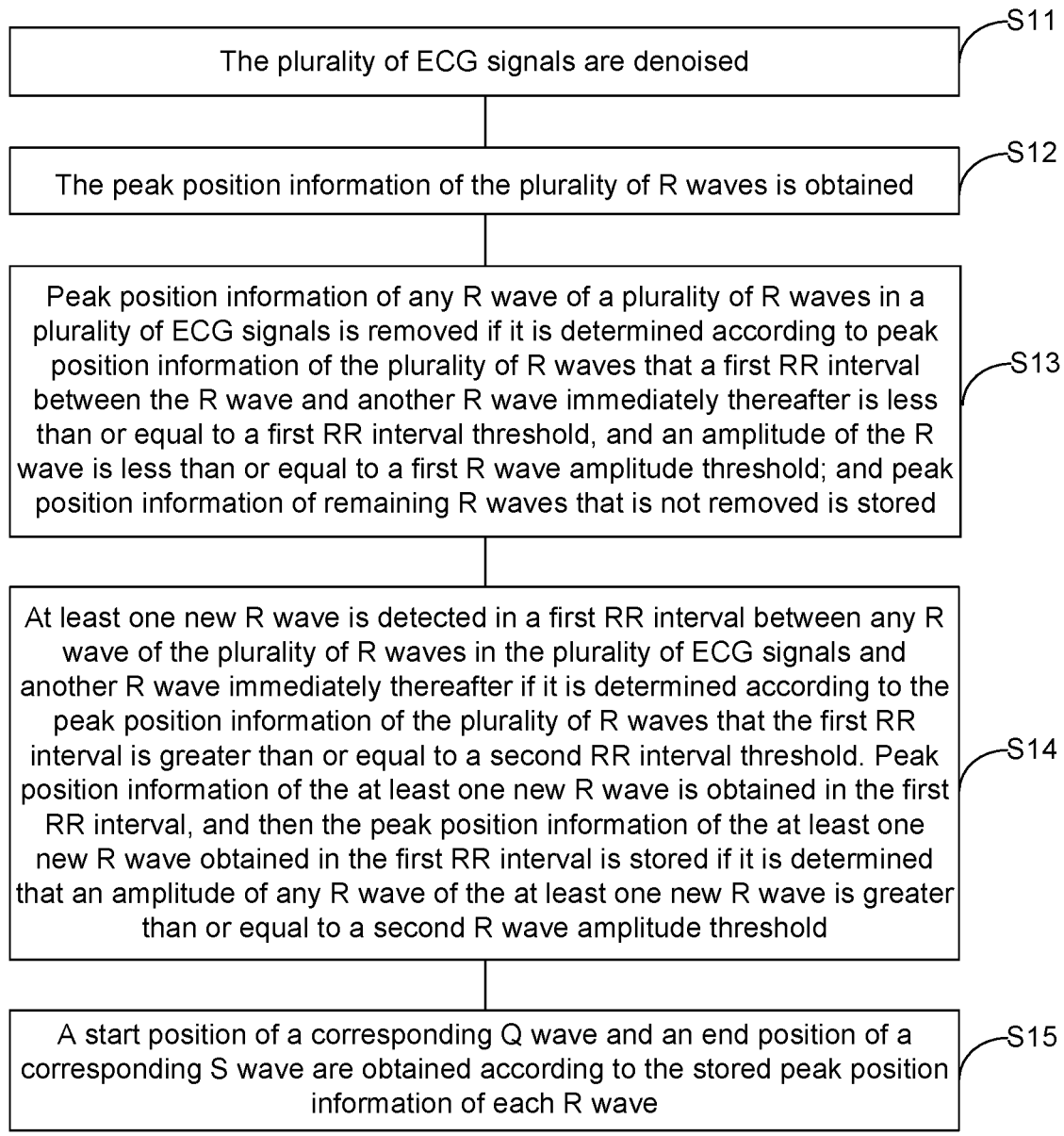
FIG. 11 is a flow chart of yet another method for processing ECG signals, in accordance with some embodiments.

In some embodiments, as shown in FIG. 11, the method further includes step 15 (S15). In S15, a start position of a Q wave corresponding to each stored R wave and an end position of an S wave corresponding to the stored R wave are obtained according to the stored peak position information of the stored R wave.

Figure 12:
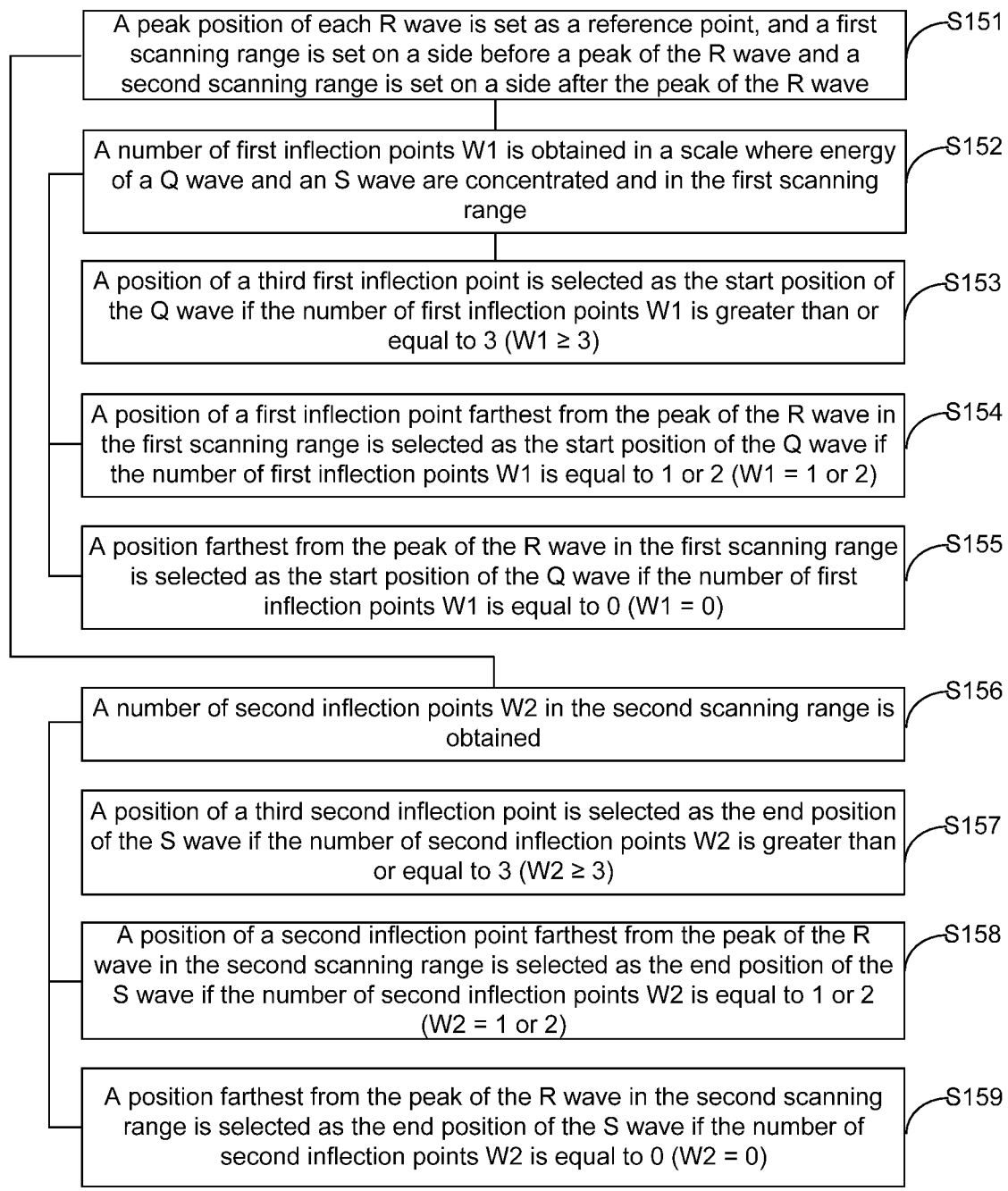
FIG. 12 is a flow chart of a method for obtaining a start position of a Q wave and an end position of an S wave, in accordance with some embodiments.

Based on this, the step of obtaining a start position of a Q wave corresponding to each stored R wave and an end position of an S wave corresponding to the stored R wave according to the stored peak position information of the stored R wave in S15 includes step 151 to step 159 (S151-S159), as shown in FIG. 12.

In S151, a peak position of each stored R wave is set as a reference point, and a first scanning range is set on a side before a peak of the R wave and a second scanning range is set on a side after the peak of the R wave.

The first scanning range and the second scanning range are both, for example, a product of 0.12 and fs (0.12×fs), wherein fs is a sampling frequency of the ECG signal. The first scanning range is the fixed number of sampling points before the peak of the R wave, and the second scanning range is the fixed number of sampling points after the peak of the R wave.

In S152, in the first scanning range, the number of first inflection points W1 is obtained at a scale where energy of the Q wave and the S wave are concentrated.

In a process of decomposing the ECG signals into four scales, energy of the Q waves and the S waves are concentrated at a scale $2^1$. An inflection point is at a non-zero point position.

In S153, a position of a third first inflection point is selected as the start position of the Q wave if the number of the first inflection points W1 is greater than or equal to 3 (W1≥3).

It will be noted that, in a case where a peak position of each R wave is set as a reference point, a first inflection point closest to the reference point is set as a first inflection point, a first inflection point second closest to the reference point is set as a second first inflection point, and the rest may be deduced by analogy.

In S154, a position of a first inflection point farthest from the peak of the R wave in the first scanning range is selected as the start position of the Q wave if the number of the first inflection points W1 is equal to 1 or 2 (W1=1 or 2).

In a case where W1 is equal to 1 (W1=1), then this first inflection point is the start position of the Q wave; in a case where W1 is equal to 2 (W1=2), then of two first inflection points, a first inflection point farther from the reference point is the start position of the Q wave.

In S155, a position farthest from the peak of the R wave in the first scanning range is selected as the start position of the Q wave if the number of first inflection points W1 is equal to 0 (W1=0).

In S156, the number of second inflection points W2 in the second scanning range is obtained.

In S157, a position of a third second inflection point is selected as the end position of the S wave if the number of the second inflection points W2 is greater than or equal to 3 (W2≥3).

It will be noted that, in a case where a peak position of each R wave is set as as a reference point, a second inflection point closest to the reference point is set as a first second inflection point, a second inflection point second closest to the reference point is set as a second inflection point, and the rest may be deduced by analogy.

In S158, a position of a second inflection point farthest from the peak of the R wave in the second scanning range is selected as the end position of the S wave if the number of the second inflection points W2 is equal to 1 or 2 (W2=1 or 2).

In a case where W2 is equal to 1 (W2=1), this second inflection point is the end position of the S wave; in a case where W2 is equal to 2 (W2=2), of two second inflection points, a second inflection point farther from the reference point is the end position of the S wave.

In S159, a position farthest from the peak of the R wave in the second scanning range is selected as the end position of the S wave if the number of the second inflection points W2 is equal to 0 (W2=0).

Some embodiments of the present disclosure provide a non-transitory computer-readable storage medium storing executable instructions that, when executed by a device, cause the device to implement the method for processing ECG signals described above. The device is, for example, an ECG machine.

Some embodiments of the present disclosure provide an apparatus for processing ECG signals. As shown in FIG. 13, the apparatus 60 includes a receiver 20, a processor 10, and at least one memory 30. The receiver 20 is coupled to the processor 10 and a recorder 40, and the processor 10 is coupled to each of the at least one memory 30.

The receiver 20 is configured to receive a plurality of ECG signals recorded by the recorder 40.

The processor 10 is configured to remove peak position information of any R wave of a plurality of R waves in the plurality of ECG signals if it is determined according to peak position information of the plurality of R waves that a first RR interval between the R wave and another R wave immediately thereafter is less than or equal to a first RR interval threshold, and an amplitude of the R wave is less than or equal to a first R wave amplitude threshold; and is configured to store peak position information of remaining R waves that is not removed in the at least one memory.

The processor 10 is further configured to: detect at least one new R wave in a first RR interval between any R wave of the plurality of R waves in the plurality of ECG signals and another R wave immediately thereafter if it is determined according to the peak position information of the plurality of R waves that the first RR interval is greater than or equal to a second RR interval threshold; and is configured to obtain peak position information of the at least one new R wave in the first RR interval, and then store the peak position information of any new R wave of the at least one new R wave obtained in the first RR interval in the at least one memory if it is determined that an amplitude of the new R wave of the at least one new R wave is greater than or equal to a second R wave amplitude threshold.

The apparatus for processing ECG signals provided by the embodiments of the present disclosure has the same advantageous effects as the method for processing ECG signals described above, and details are not described herein again.

In some embodiments, as shown in FIG. 13, the processor 10 is further configured to denoise the plurality of ECG signals to obtain denoised ECG signals.

The processor 10 is configured to obtain peak position information of the plurality of R waves according to the denoised ECG signals.

In some embodiments, the processor 10 is further configured to: decomposing the denoised ECG signals into components that appear at N scales by using a quadratic spline wavelet, wherein N is greater than or equal to 4 (N≥4); obtain pairs of positive maximum and negative maximum at a scale $2^j$, wherein the scale $2^j$ is a scale where energy of a QRS complex is concentrated, and j is greater than 1 and less than N (1<j<N); convert data of all pairs of positive maximum and negative maximum at the scale $2^j$ into a first matrix with a fixed time length; select at least one pair of positive maximum and negative maximum, in which a positive maximum is greater than or equal to a first preset value and a negative maximum is less than or equal to a second preset value, from each row of the first matrix; and obtain peak position information of a R wave according to a zero-crossing position and a time shift between a positive maximum and a negative maximum in each selected pair of positive maximum and negative maximum, wherein the time shift is $$\frac{2^j - 1}{2}.$$

Based on this, in some embodiments, each row in the first matrix corresponds to a set of a first preset value and a second preset value. The first preset value corresponding to the i-th row is $$A(i) = k0 \times \frac{Ai_{max1} + Ai_{max2}}{2},$$

the second preset value corresponding to the i-th row is $$B(i) = k0 \times \frac{Bi_{min1} + Bi_{min2}}{2};$$

wherein i is a row number of the first matrix.

$Ai_{max1}$ is the largest value in data at and before a $$\frac{M1}{2}\text{-}th$$

second in the i-th row, $Ai_{max2}$ is the largest value in data after the $$\frac{M1}{2}\text{-}th$$

second in the i-th row, $Bi_{min1}$ is the smallest value in data at and before the $$\frac{M1}{2}\text{-}th$$

second in the i-th row, and $Bi_{min2}$ is the smallest value after the $$\frac{M1}{2}\text{-}th$$

second in the i-th row; wherein k0 is a scale factor less than 1, and M1 is a time length of each row of data. In some embodiments, M1 is an even number.

It will be noted that, as for an identification process of the processor 10, reference may be made to description of obtaining the peak position information of R waves in the method for processing ECG signals above, and details are not described herein again.

In some embodiments, the processor 10 is further configured to: convert data of the denoised ECG signals into a second matrix with a fixed time length; calculate an RR interval mean value $RR(p)_{mean}$ of each row in the second matrix and an amplitude mean value $Rh(p)$ of each row in the second matrix according to the peak position information of the plurality of R waves, wherein p is a row number of the second matrix; set $k1 \times RR(p)_{mean}$ as a first RR interval threshold of the p-th row and $k2 \times Rh(p)$ as a first R wave amplitude threshold of the p-th row, wherein k1 and k2 are both scale factors less than 1; and remove peak position information of any R wave of R waves in the p-th row if it is determined according to peak position information of the R waves in the p-th row that a first RR interval between the R wave and another R wave immediately thereafter is less than or equal to the first RR interval threshold of the p-th row, and an amplitude of the R wave is less than or equal to the first R wave amplitude threshold of the p-th row.

In some embodiments, the processor 10 is further configured to: set $k3 \times RR(p)_{mean}$ as a second RR interval threshold of the p-th row, wherein k3 is a scale factor greater than 1; obtain at least one pair of positive maximum and negative maximum, in which a positive maximum is greater than or equal to a third preset value and a negative maximum is less than or equal to a fourth preset value, in a first RR interval between any R wave of the R waves in the p-th row and another R wave immediately thereafter if it is determined according to the peak position information of the R waves in the p-th row that the first RR interval is greater than or equal to the second RR interval threshold of the p-th row, so as to obtain peak position information of the at least one new R wave, wherein the third preset value is less than the first preset value, and an absolute value of the fourth preset value is less than an absolute value of the second preset value; set $k4 \times Rh(p)$ as a second R wave amplitude threshold of the p-th row, wherein k4 is a scale factor less than 1; obtain peak position information of the at least one new R wave in the first RR interval in the p-th row, and then store the peak position information of any one of the at least one new R wave obtained in the first RR interval in the at least one memory if it is determined that an amplitude of the one of the at least one new R wave is greater than or equal to the second R wave amplitude threshold of the p-th row.

It will be noted that, as for the determination process of the processor 10, reference may be made to description of the method for processing ECG signals above, and details are not described herein again.

In some embodiments, as shown in FIG. 13, the processor 10 is configured to obtain a start position of a corresponding Q wave and an end position of a corresponding S wave according to the stored peak position information of each R wave.

As for how to obtain the start position of the Q wave and the end position of the S wave, reference may be made to description of the method for processing ECG signals above, and details are not described herein again.

It will be noted that, scale factors mentioned in embodiments of the present disclosure are all greater than zero.

A person of ordinary skill in the art can understand that: all or part of the steps in the method embodiments described above may be implemented by using a program to control related hardware to perform the steps. The foregoing program may be stored in a non-transitory computer-readable storage medium for executing the steps included in the method embodiments above. The foregoing storage medium includes various media well known in the art that can store program codes, such as a read-only memory (ROM), a random-access memory (RAM), a register, a magnetic disk, or an optical disk. An exemplary storage medium is coupled to the processor to enable the processor to read information from, and write information to, the storage medium. The processor may be a central processing unit (CPU), a field programmable logic array (FPGA), a microprogrammed control unit (MCU), an application specific integrated circuit (ASIC), or any device having logic computing capabilities and/or program execution capabilities. The recorder is a device for detecting and collecting ECG signals. The recorder may be a recording circuit and device commonly used in the field, and is not limited to a medical ECG lead collector, a portable collector, a patch collector, a sports bracelet, and a smart watch. An implementation form of the above device is not limited herein. The receiver is a device for receiving an ECG signal. The receiver and the recorder may communicate via Bluetooth, circuit, NFC, WiFi or infrared ray. An implementation form of the device is not limited herein.

Figure 14:
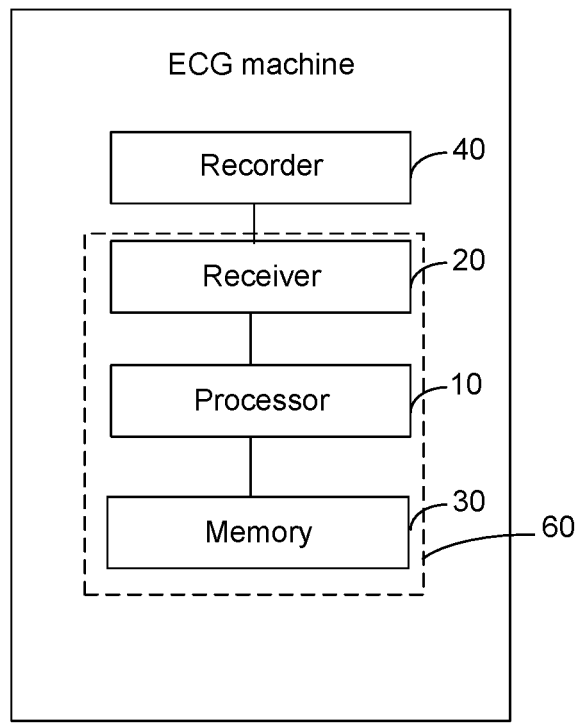
FIG. 14 is a schematic diagram of an ECG machine, in accordance with some embodiments.

Some embodiments of the present disclosure provide an ECG machine which, as shown in FIG. 14, includes a recorder 40 and the apparatus for processing ECG signals 60 described by the foregoing embodiments. The recorder 40 is configured to record a plurality of ECG signals. The apparatus for processing ECG signals 60 is configured to process the plurality of ECG signals.

The foregoing descriptions are merely some implementation manners of the present disclosure, but the protection scope of the present disclosure is not limited thereto. Any person skilled in the art could readily conceive of changes or replacements within the technical scope of the present disclosure, which shall all be included in the protection scope of the present disclosure. Therefore, the protection scope of the present disclosure shall be subject to the protection scope of the claims.

What is claimed is:

1. A method for processing electrocardiogram (ECG) signals, comprising:
    removing peak position information of any R wave of a plurality of R waves in a plurality of ECG signals if it is determined, according to peak position information of the plurality of R waves that a first RR interval between the R wave and another R wave immediately thereafter is less than or equal to a first RR interval threshold, and an amplitude of the R wave is less than or equal to a first R wave amplitude threshold; storing peak position information of remaining R waves that is not removed;
    detecting at least one new R wave in a first RR interval between any R wave of the plurality of R waves in the plurality of ECG signals and another R wave immediately thereafter if it is determined according to the peak position information of the plurality of R waves that the first RR interval is greater than or equal to a second RR interval threshold; obtaining peak position information of the at least one new R wave in the first RR interval, and then storing the peak position information of any new R wave of the at least one new R wave obtained in the first RR interval if it is determined that an amplitude of the new R wave of the at least one new R wave is greater than or equal to a second R wave amplitude threshold; and
    obtaining a start position of a corresponding Q wave and an end position of a corresponding S wave according to stored peak position information of each R wave, wherein
    obtaining a start position of a corresponding Q wave and an end position of a corresponding S wave according to the stored peak position information of each R wave includes:
    setting a peak position of each R wave as a reference point, and setting a first scanning range on a side before a peak of the R wave and a second scanning range on a side after the peak of the R wave;
    obtaining, in the first scanning range, a number of first inflection points W1 at a scale where energies of the Q wave and the S wave are concentrated;
    selecting a position of a third first inflection point as the start position of the Q wave if the number of first inflection points W1 is greater than or equal to 3;
    selecting a position of a first inflection point farthest from the peak of the R wave in the first scanning range as the start position of the Q wave if the number of first inflection points W1 is equal to 1 or 2;
    selecting a position farthest from the peak of the R wave in the first scanning range as the start position of the Q wave if the number of first inflection points W1 is equal to 0;
    obtaining a number of second inflection points W2 in the second scanning range;
    selecting a position of a third second inflection point as the end position of the S wave if the number of second inflection points W2 is greater than or equal to 3;
    selecting a position of a second inflection point farthest from the peak of the R wave in the second scanning range as the end position of the S wave if the number of second inflection points W2 is equal to 1 or 2; and
    selecting a position farthest from the peak of the R wave in the second scanning range as the end position of the S wave if the number of second inflection points W2 is equal to 0.

2. The method according to claim 1, further comprising:
    denoising the plurality of ECG signals to obtain denoised ECG signals; and
    obtaining peak position information of the plurality of R waves according to the denoised ECG signals.

3. The method according to claim 2, wherein obtaining peak position information of the plurality of R waves includes:
    decomposing the denoised ECG signals into components that appear at N scales by using a quadratic spline wavelet, wherein N is greater than or equal to 4;
    obtaining pairs of positive maximum and negative maximum at a scale $2^j$, wherein the scale $2^j$ is a scale where energy of a QRS complex is concentrated, and j is greater than 1 and less than N;
    converting data of all pairs of positive maximum and negative maximum at the scale $2^j$ into a first matrix with a fixed time length;
    selecting at least one pair of positive maximum and negative maximum, in which a positive maximum is greater than or equal to a first preset value and a negative maximum is less than or equal to a second preset value, from each row of the first matrix; and
    obtaining peak position information of a R wave according to a zero-crossing position and a time shift between a positive maximum and a negative maximum in each selected pair of positive maximum and negative maximum, wherein the time shift is $$\frac{2^j - 1}{2}.$$

4. The method according to claim 3, wherein each row of the first matrix has a plurality of data, and each row of the first matrix corresponds to a set of a first preset value and a second preset value;
a first preset value corresponding to an i-th row is $$A(i) = k0 \times \frac{Ai_{max1} + Ai_{max2}}{2},$$

a second preset value corresponding to the i-th row is $$B(i) = k0 \times \frac{Bi_{min1} + Bi_{min2}}{2},$$

wherein i is a row number of the first matrix;

$Ai_{max1}$ is the largest value of a datum in data corresponding to a time length from 0 to $$\frac{M1}{2}\text{-}th$$

second in the i-th row, $Ai_{max2}$ is the largest value of a datum in data corresponding to a time length from the $$\frac{M1}{2}\text{-}th$$

second to M1-th second in the i-th row, $Bi_{min1}$ is the smallest value of a datum in data corresponding to the time length from 0 to the $$\frac{M1}{2}\text{-}th$$

second in the i-th row, and $Bi_{min2}$ is the smallest value of a datum in data corresponding to the time length from the $$\frac{M1}{2}\text{-}th$$

second to the M1-th second in the i-th row, wherein k0 is a scale factor less than 1, and M1 is a time length of each row of data, the time length from 0 to $$\frac{M1}{2}\text{-}th$$

second includes moments of 0 and the $$\frac{M1}{2}\text{-}th$$

second and the time length from the $$\frac{M1}{2}\text{-}th$$

second to M1-th second includes a moment of the M1-th second.

5. The method according to claim 2, wherein, removing peak position information of any R wave of a plurality of R waves in a plurality of ECG signals if it is determined according to peak position information of the plurality of R waves that a first RR interval between the R wave and another R wave immediately thereafter is less than or equal to a first RR interval threshold, and an amplitude of the R wave is less than or equal to a first R wave amplitude threshold includes:
   converting data of the denoised ECG signals into a second matrix with a fixed time length;
   calculating an RR interval mean value $RR(p)_{mean}$ of each row in the second matrix and an amplitude mean value $Rh(p)$ of each row in the second matrix according to the peak position information of the plurality of R waves, wherein p is a row number of the second matrix;
   setting a product of k1 and $RR(p)_{mean}$ as a first RR interval threshold of the p-th row and a product of k2 and $Rh(p)$ as a first R wave amplitude threshold of the p-th row, wherein k1 and k2 are both scale factors less than 1; and
   removing peak position information of any R wave of R waves in the p-th row if it is determined according to peak position information of the R waves in the p-th row that a first RR interval between the R wave and another R wave immediately thereafter is less than or equal to the first RR interval threshold of the p-th row, and an amplitude of the R wave is less than or equal to the first R wave amplitude threshold of the p-th row.

6. The method according to claim 5, wherein removing at least one new R wave in a first RR interval between any R wave of the plurality of R waves in the plurality of ECG signals and another R wave immediately thereafter if it is determined according to the peak position information of the plurality of R waves that the first RR interval is greater than or equal to a second RR interval threshold includes:
   setting a product of k3 and $RR(p)_{mean}$ as a second RR interval threshold of the p-th row, wherein k3 is a scale factor greater than 1;
   obtaining at least one pair of positive maximum and negative maximum, in which a positive maximum is greater than or equal to a third preset value and a negative maximum is less than or equal to a fourth preset value, in the first RR interval between any R wave of the R waves in the p-th row and another R wave immediately thereafter if it is determined according to the peak position information of the R waves in the p-th row that the first RR interval is greater than or equal to the second RR interval threshold of the p-th row, so as to obtain peak position information of the at least one new R wave, wherein
   the third preset value is less than a first preset value, and an absolute value of the fourth preset value is less than an absolute value of a second preset value.

7. The method according to claim 6, wherein obtaining peak position information of the at least one new R wave in the first RR interval, and then storing the peak position information of any new R wave of the at least one new R wave obtained in the first RR interval if it is determined that an amplitude of the new R wave of the at least one new R wave is greater than or equal to a second R wave amplitude threshold includes:
   setting a product of k4 and $Rh(p)$ as a second R wave amplitude threshold of the p-th row, wherein k4 is a scale factor less than 1;
   obtaining peak position information of the at least one new R wave in the first RR interval in the p-th row, and then storing peak position information of any new R wave of the at least one new R wave obtained in the first RR interval if it is determined that an amplitude of the new R wave of the at least one new R wave is greater than or equal to the second R wave amplitude threshold of the p-th row.

8. The method according to claim 2, wherein denoising the plurality of ECG signals includes:
   performing wavelet decomposition on the plurality of ECG signals;
   using a filtering method of threshold processing to remove a high frequency noise in the plurality of ECG signals;

using a zeroing method to remove low frequency baseline drift in the plurality of ECG signals;
reconstructing the ECG signals to obtain denoised ECG signals.

9. An apparatus for processing electrocardiogram (ECG) signals, the apparatus comprising a receiver, a processor, and at least one memory, wherein
the receiver is configured to receive a plurality of ECG signals recorded by a recorder;
the processor is configured to:
remove peak position information of any R wave of a plurality of R waves in a plurality of ECG signals if it is determined, according to peak position information of the plurality of R waves that a first RR interval between the R wave and another R wave immediately thereafter is less than or equal to a first RR interval threshold, and an amplitude of the R wave is less than or equal to a first R wave amplitude threshold; store peak position information of remaining R waves that is not removed in the at least one memory;
detect at least one new R wave in a first RR interval between any R wave of the plurality of R waves in the plurality of ECG signals and another R wave immediately thereafter if it is determined according to the peak position information of the plurality of R waves that the first RR interval is greater than or equal to a second RR interval threshold; obtain peak position information of the at least one new R wave in the first RR interval, and then store the peak position information of any new R wave of the at least one new R wave obtained in the first RR interval in the at least one memory if it is determined that an amplitude of the new R wave of the at least one new R wave is greater than or equal to a second R wave amplitude threshold; and
obtain a start position of a corresponding Q wave and an end position of a corresponding S wave according to the stored peak position information of each R wave, wherein
the processor being configured to obtain a start position of a corresponding Q wave and an end position of a corresponding S wave according to the stored peak position information of each R wave includes:
the processor being further configured to:
set a peak position of each R wave as a reference point, and setting a first scanning range on a side before a peak of the R wave and a second scanning range on a side after the peak of the R wave;
obtain, in the first scanning range, a number of first inflection points W1 at a scale where energies of the Q wave and the S wave are concentrated;
select a position of a third first inflection point as the start position of the Q wave if the number of first inflection points W1 is greater than or equal to 3;
select a position of a first inflection point farthest from the peak of the R wave in the first scanning range as the start position of the Q wave if the number of first inflection points W1 is equal to 1 or 2;
select a position farthest from the peak of the R wave in the first scanning range as the start position of the Q wave if the number of first inflection points W1 is equal to 0;
obtain a number of second inflection points W2 in the second scanning range;
select a position of a third second inflection point as the end position of the S wave if the number of second inflection points W2 is greater than or equal to 3;
select a position of a second inflection point farthest from the peak of the R wave in the second scanning range as the end position of the S wave if the number of second inflection points W2 is equal to 1 or 2; and
select a position farthest from the peak of the R wave in the second scanning range as the end position of the S wave if the number of second inflection points W2 is equal to 0.

10. The apparatus for processing ECG signals according to claim 9, wherein the processor is further configured to:
denoise the plurality of ECG signals to obtain denoised ECG signals; and
obtain peak position information of the plurality of R waves according to the denoised ECG signals.

11. The apparatus for processing ECG signals according to claim 10, wherein the processor is further configured to:
decompose the denoised ECG signals into components that appear at N scales by using a quadratic spline wavelet, wherein N is greater than or equal to 4;
obtain pairs of positive maximum and negative maximum at a scale $2^j$, wherein the scale $2^j$ is a scale where energy of a QRS complex is concentrated, and j is greater than 1 and less than N;
convert data of all pairs of positive maximum and negative maximum at the scale $2^j$ into a first matrix with a fixed time length;
select at least one pair of positive maximum and negative maximum, in which a positive maximum is greater than or equal to a first preset value and a negative maximum is less than or equal to a second preset value, from each row of the first matrix; and
obtain peak position information of a R wave according to a zero-crossing position and a time shift between a positive maximum and a negative maximum in each selected pair of positive maximum and negative maximum,
wherein the time shift is $$\frac{2^j - 1}{2}.$$

12. The apparatus for processing ECG signals according to claim 11, wherein each row of the first matrix has a plurality of data, and each row of the first matrix corresponds to a set of a first preset value and a second preset value;
a first preset value corresponding to an i-th row is $$A(i) = k0 \times \frac{Ai_{max1} + Ai_{max2}}{2},$$

a second preset value corresponding to the i-th row is $$B(i) = k0 \times \frac{Bi_{min1} + Bi_{min2}}{2},$$

wherein i is a row number of the first matrix;
$Ai_{max1}$ is the largest value of a datum in data corresponding to a time length from 0 to $$\frac{M1}{2}\text{-}th$$

second in the i-th row, $Ai_{max2}$ is the largest value of a datum in data corresponding to a time length from the $$\frac{M1}{2}\text{-}th$$

second to M1-th second in the i-th row, $Bi_{min1}$ is the smallest value of a datum in data corresponding to the time length from 0 to the $$\frac{M1}{2}\text{-}th$$

second in the i-th row, and $Bi_{min2}$ is the smallest value of a datum in data corresponding to the time length from the $$\frac{M1}{2}\text{-}th$$

second to the M1-th second in the i-th row; wherein k0 is a scale factor less than 1, and M1 is a time length of each row of data, the time length from 0 to $$\frac{M1}{2}\text{-}th$$

second includes moments of 0 and the $$\frac{M1}{2}\text{-}th$$

second and the time length from the $$\frac{M1}{2}\text{-}th$$

second to M1-th second includes a moment of the M1-th second.

13. The apparatus for processing ECG signals according to claim 10, wherein the processor is further configured to:
convert data of the set of denoised ECG signals into a second matrix with a fixed time length;
calculate an RR interval mean value $RR(p)_{mean}$ of each row in the second matrix and an amplitude mean value $Rh(p)$ of each row in the second matrix according to the peak position information of the plurality of R waves, wherein p is a row number of the second matrix;
set a product of k1 and $RR(p)_{mean}$ as a first RR interval threshold of the p-th row and a product of k2 and $Rh(p)$ as a first R wave amplitude threshold of the p-th row, wherein k1 and k2 are both scale factors less than 1; and
remove peak position information of any R wave of R waves in the p-th row if it is determined according to peak position information of the R waves in the p-th row that a first RR interval between the R wave and another R wave immediately thereafter is less than or equal to the first RR interval threshold of the p-th row, and an amplitude of the R wave is less than or equal to the first R wave amplitude threshold of the p-th row.

14. The apparatus for processing ECG signals according to claim 13, wherein the processor is further configured to:
set a product of k3 and $RR(p)_{mean}$ as a second RR interval threshold of the p-th row, wherein k3 is a scale factor greater than 1;
obtain at least one pair of positive maximum and negative maximum, in which a positive maximum is greater than or equal to a third preset value and a negative maximum is less than or equal to a fourth preset value, in the first RR interval between any R wave of the plurality of R waves in the p-th row and another R wave immediately thereafter if it is determined according to the peak position information of the R waves in the p-th row that the first RR interval is greater than or equal to the second RR interval threshold of the p-th row, so as to obtain peak position information of the at least one new R wave, wherein the third preset value is less than the first preset value, and an absolute value of the fourth preset value is less than an absolute value of the second preset value;
set a product of k4 and $Rh(p)$ as a second R wave amplitude threshold of the p-th row, wherein k4 is a scale factor less than 1;
obtain peak position information of the at least one new R wave in the first RR interval in the p-th row, and then store peak position information of any new R wave of the at least one new R wave obtained in the first RR interval in the at least one memory if it is determined that an amplitude of the new R wave of the at least one new R wave is greater than or equal to the second R wave amplitude threshold of the p-th row.

15. A non-transitory computer-readable storage medium storing executable instructions that, when executed by an electrocardiogram device, cause the electrocardiogram device to implement the method according to claim 1.

16. An electrocardiogram (ECG) machine, comprising:
a recorder configured to record a plurality of ECG signals; and
the apparatus for processing ECG signals according to claim 9 configured to process the plurality of ECG signals.

* * * * *